(12) United States Patent
Vaders et al.

(10) Patent No.: US 11,241,274 B2
(45) Date of Patent: Feb. 8, 2022

(54) ELECTRICALLY INSULATIVE ELECTRODE SPACERS, AND RELATED DEVICES, SYSTEMS, AND METHODS

(71) Applicant: Intuitive Surgical Operations, Inc., Sunnyvale, CA (US)

(72) Inventors: Dennis H. Vaders, West Haven, CT (US); Stuart Taylor, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1107 days.

(21) Appl. No.: 15/800,252

(22) Filed: Nov. 1, 2017

(65) Prior Publication Data
US 2018/0125569 A1 May 10, 2018

Related U.S. Application Data

(60) Provisional application No. 62/417,567, filed on Nov. 4, 2016.

(51) Int. Cl.
*A61B 18/14* (2006.01)
*B29C 70/76* (2006.01)
(Continued)

(52) U.S. Cl.
CPC .......... *A61B 18/1445* (2013.01); *B29C 65/62* (2013.01); *B29C 70/76* (2013.01); *A61B 34/30* (2016.02); *A61B 2017/00526* (2013.01); *A61B 2017/2926* (2013.01); *A61B 2018/0063* (2013.01); *A61B 2018/00083* (2013.01); *A61B 2018/00136* (2013.01); *A61B 2018/00577* (2013.01); *A61B 2018/00595* (2013.01); *A61B 2018/00601* (2013.01);
(Continued)

(58) Field of Classification Search
CPC ...... A61B 18/1445; A61B 2018/00083; A61B 2018/00136; A61B 2018/00577; A61B 2018/00595; A61B 2018/00601; A61B 2018/00619; A61B 2018/0063; A61B 2018/1455; A61B 2018/146; B29C 65/62; B29C 70/76
See application file for complete search history.

(56) References Cited

U.S. PATENT DOCUMENTS 5,891,142 A 4/1999 Eggers et al.
8,361,071 B2 1/2013 Tetzlaff et al.
(Continued)

OTHER PUBLICATIONS

Schlick C.M., "Industrial Engineering and Ergonomics," Vision, Concepts, Methods and Tool, 2009, 727 pages.
(Continued)

*Primary Examiner* — Daniel W Fowler
*Assistant Examiner* — Bo Ouyang
(74) *Attorney, Agent, or Firm* — Jones Robb, PLLC

(57) ABSTRACT

An electrode assembly comprises an electrode support, an electrode on the electrode support, the electrode having a working surface extending generally transverse to a thickness of the electrode, and a filament of electrically insulative material overlying a portion of the working surface of the electrode and at least partially extending through the thickness of the electrode. An electrosurgical may include an end effector having a jaw member comprising such an electrode assembly.

19 Claims, 17 Drawing Sheets

(51) Int. Cl.
  *B29C 65/62*  (2006.01)
  *A61B 18/00*  (2006.01)
  *B29L 31/00*  (2006.01)
  *A61B 17/29*  (2006.01)
  *A61B 17/00*  (2006.01)
  *A61B 34/30*  (2016.01)

(52) U.S. Cl.
  CPC .............. *A61B 2018/00619* (2013.01); *A61B 2018/146* (2013.01); *A61B 2018/1455* (2013.01); *B29L 2031/7546* (2013.01)

(56) References Cited

U.S. PATENT DOCUMENTS

| | | | |
|---|---|---|---|
| 8,858,547 | B2 | 10/2014 | Brogna |
| 8,939,975 | B2 | 1/2015 | Twomey et al. |
| 9,055,961 | B2 | 6/2015 | Manzo et al. |
| 2004/0122423 | A1 | 6/2004 | Dycus et al. |
| 2004/0236325 | A1* | 11/2004 | Tetzlaff .............. A61B 18/1445 606/51 |
| 2013/0325031 | A1 | 12/2013 | Schena et al. |
| 2013/0325033 | A1 | 12/2013 | Schena et al. |
| 2016/0235463 | A1* | 8/2016 | Ogata .................. A61B 18/042 |
| 2017/0196618 | A1 | 7/2017 | Scholer et al. |
| 2017/0238990 | A1 | 8/2017 | Soni |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

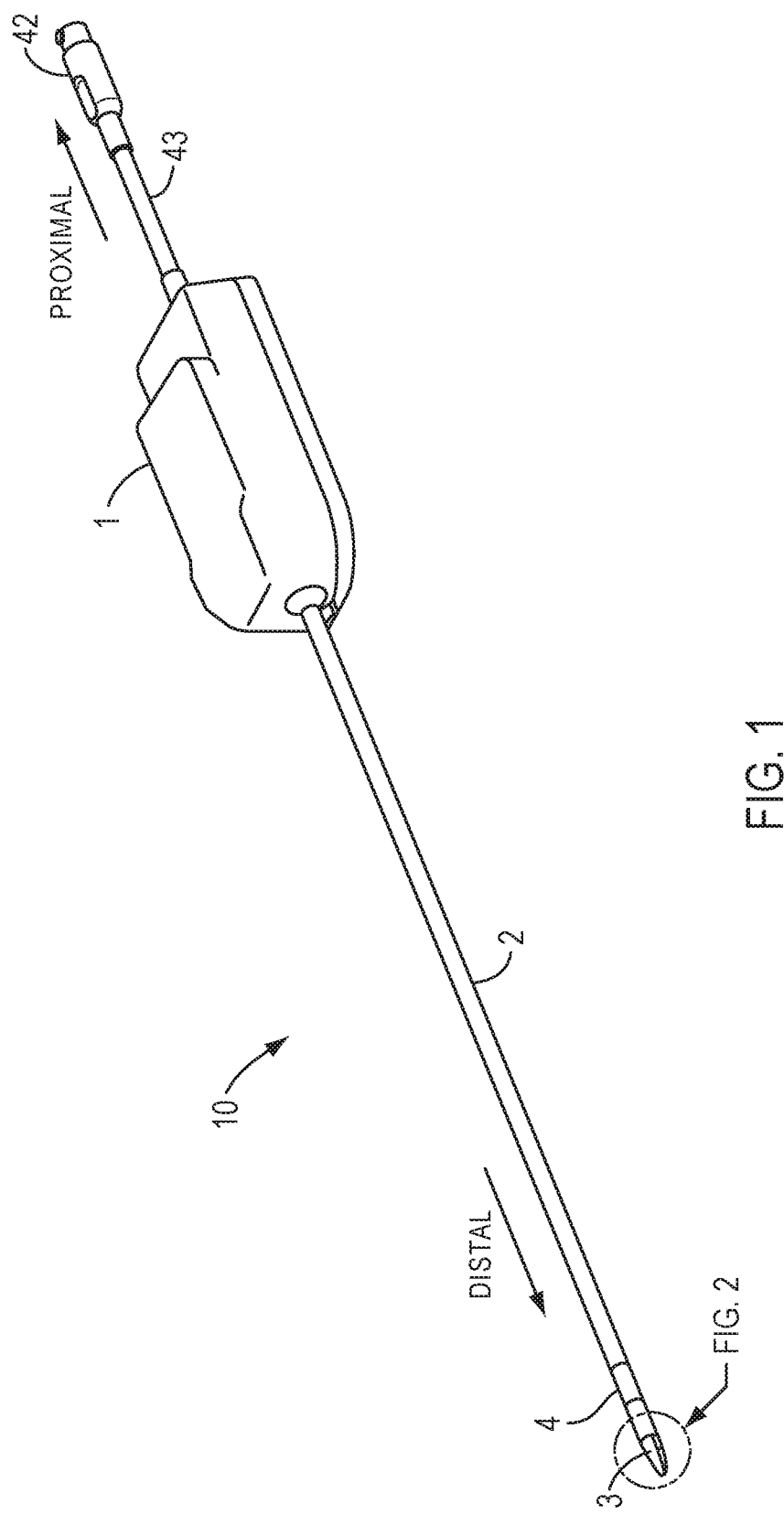

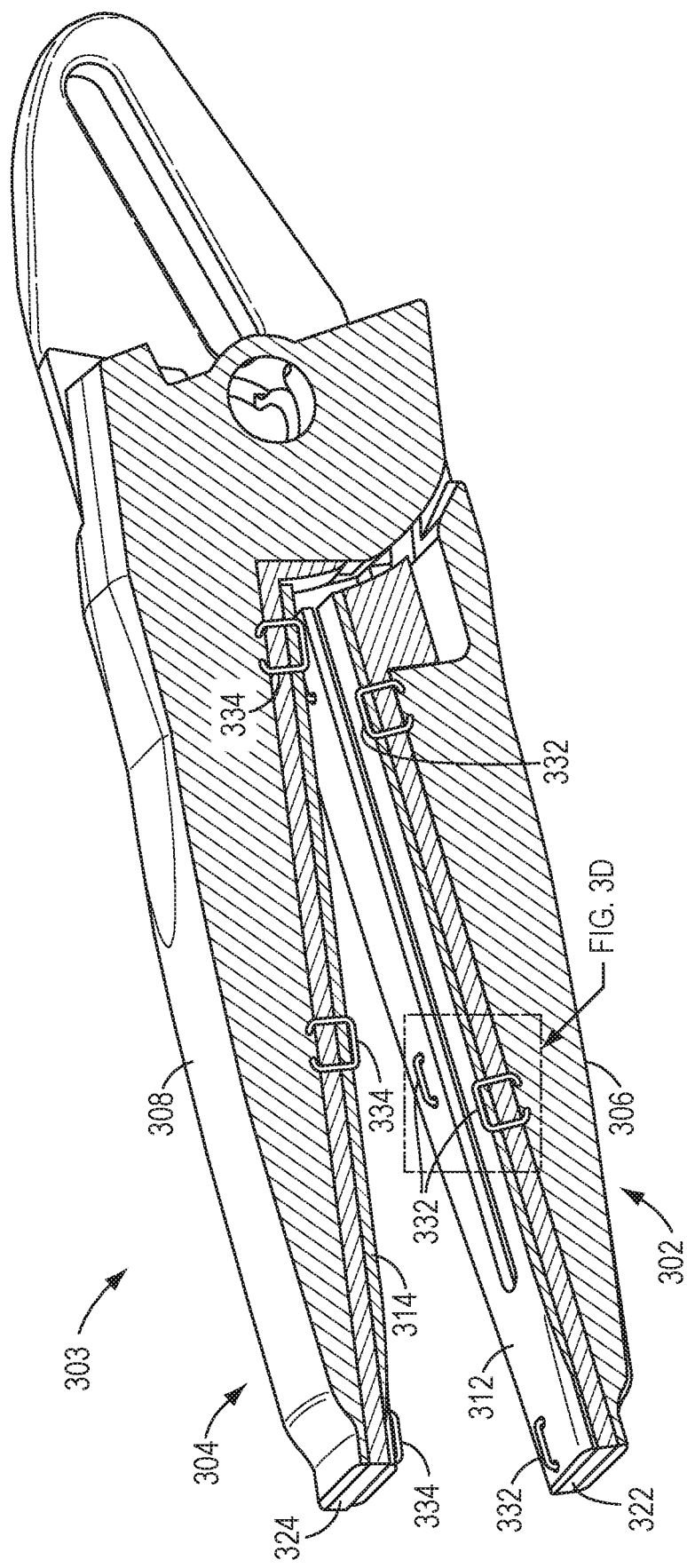

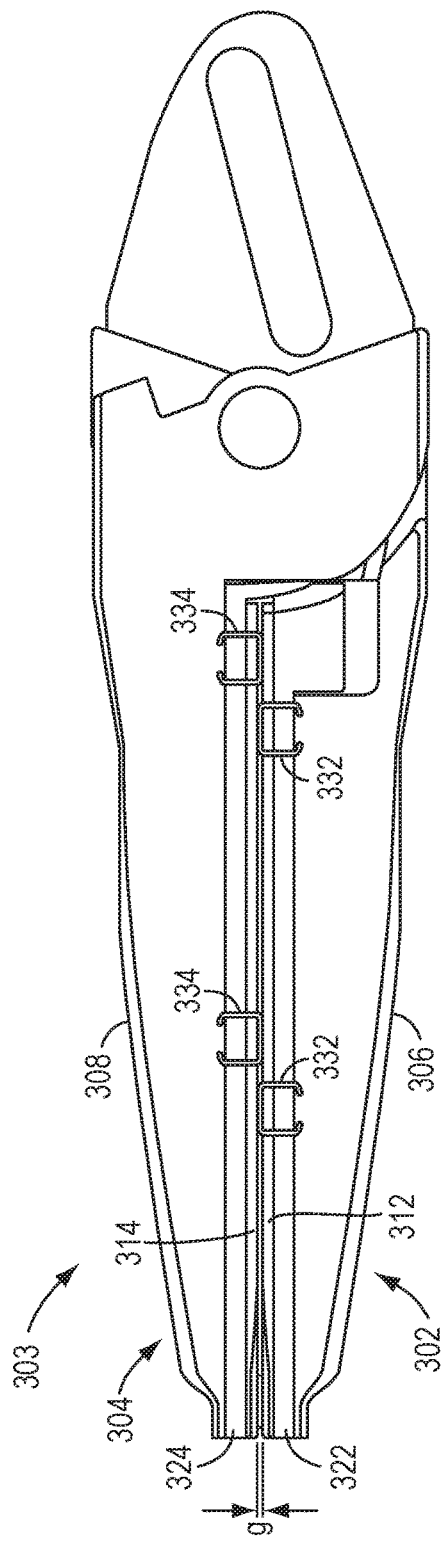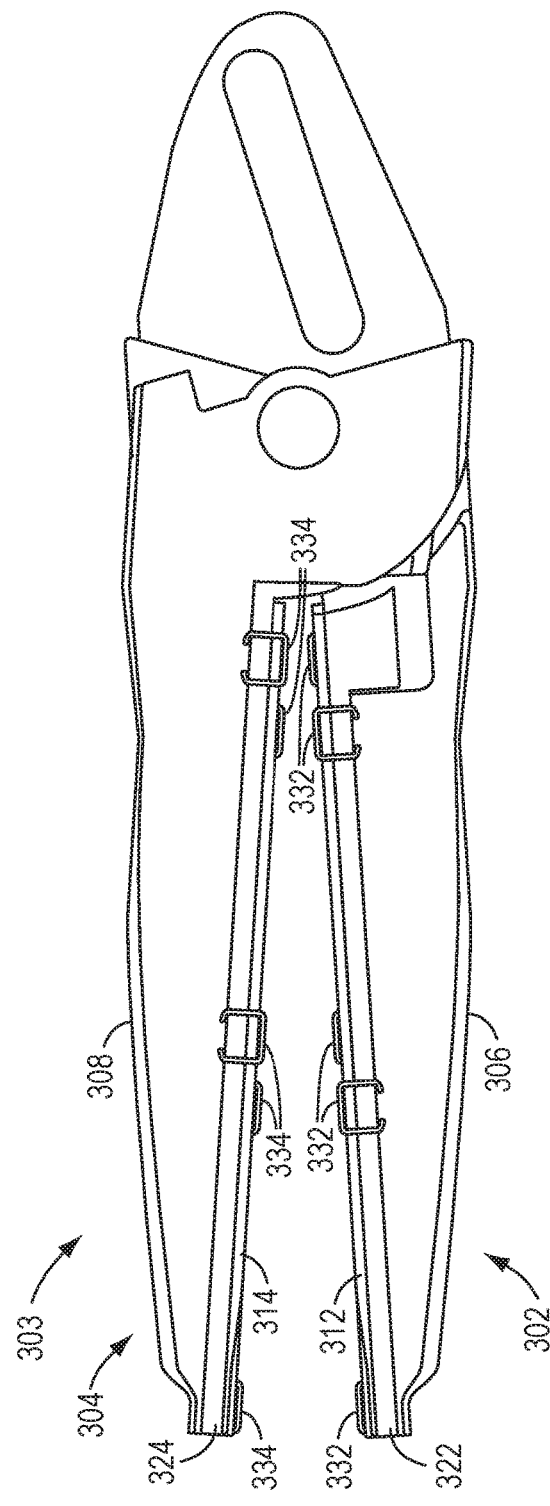
FIG. 3B
FIG. 3C

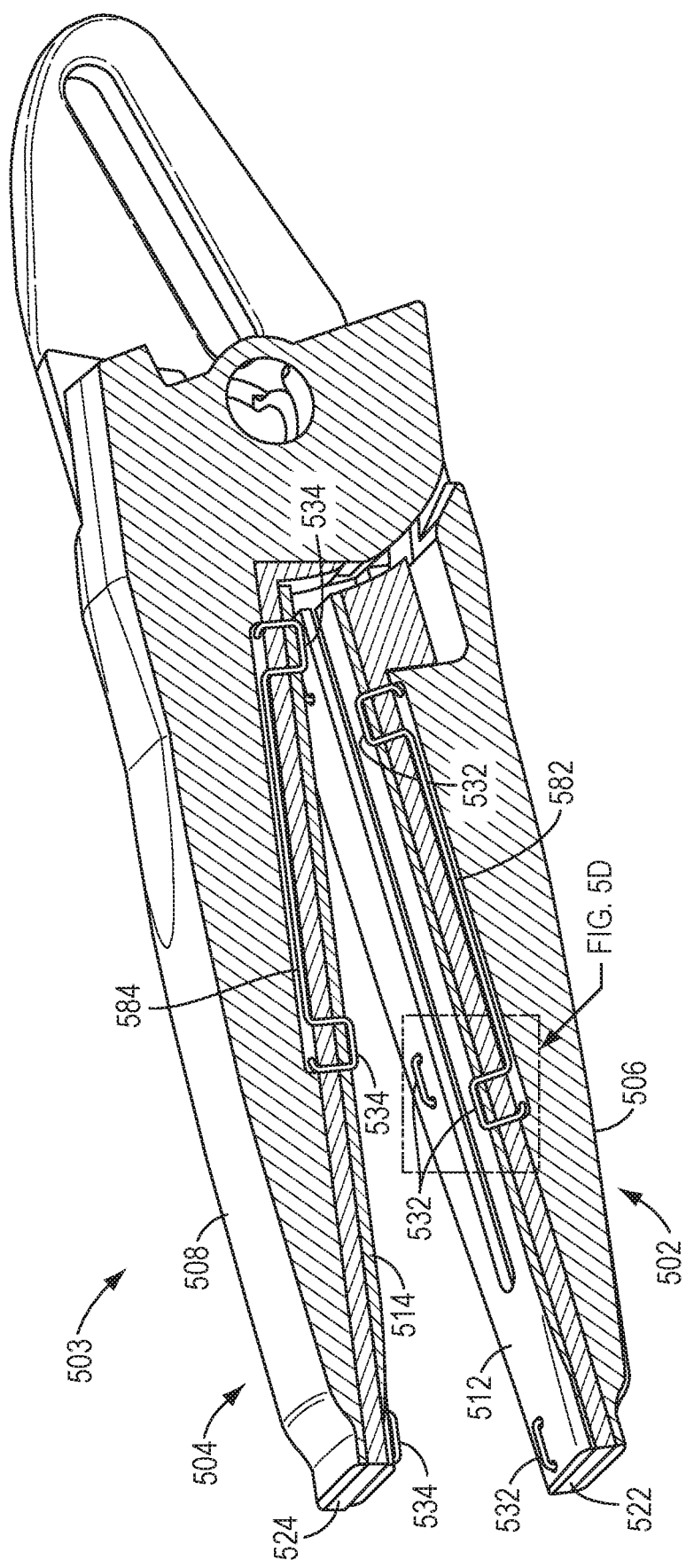

ELECTRICALLY INSULATIVE ELECTRODE SPACERS, AND RELATED DEVICES, SYSTEMS, AND METHODS

RELATED APPLICATIONS

This application claims priority to Provisional U.S. Patent Application No. 62/417,567, filed on Nov. 4, 2016, which is incorporated by reference herein in its entirety.

This application is related to U.S. patent application Ser. No. 15/800,248, filed on Nov. 1, 2017 (now U.S. Pat. No. 11,040,189), which claims priority to Provisional U.S. Patent Application No. 62/417,561, entitled "ELECTRODE ASSEMBLIES WITH ELECTRICALLY INSULATIVE ELECTRODE SPACERS, AND RELATED DEVICES, SYSTEMS, AND METHODS," filed on Nov. 4, 2017, the entire contents of each of which are incorporated by reference herein.

TECHNICAL FIELD

The present disclosure relates generally to electrically insulative spacers used to separate opposing electrode assemblies. More specifically, the present disclosure relates to electrically insulative spacers and electrode assemblies for electrical flux delivery instruments, such as, for example, electrosurgical instruments, and related systems and methods.

INTRODUCTION

An electrical flux delivery instrument can have various configurations. In some configurations, an electrical flux delivery instrument has two separated electrodes configured as parts of opposing jaw members that are operably coupled to grip material between the electrodes. In operation, an electrical flux delivery instrument treats the material layers sandwiched by the electrodes by passing energy between the electrodes so as to heat-fuse (e.g., seal) the material layers. Generally, one or more spacers made from insulative material are used to maintain a requisite degree of separation (i.e., a gap) between a surface of an electrode and an opposing surface, such as the surface of an opposing electrode. Where the opposing surface is a surface of the other electrode, such spacers can prevent a short circuit by impeding (e.g., preventing) the electrode surfaces from being driven into mutual contact. Spacers can also prevent undesirable electrical arcing by keeping surfaces of opposing electrodes sufficiently spaced from one another.

In the context of the electrical flux delivery instrument being an electrosurgical instrument, energy, such as, for example, bipolar energy, passed between electrodes is used to deliver electrical energy so as to fuse or cauterize tissue. Tissue or other body parts can be gripped between two electrodes of an end effector at the distal end of an electrosurgical instrument, and electrosurgical energy can be passed between the electrodes in order to fuse or otherwise heat-treat the grasped tissue. An example of such tissue fusing includes fusing together opposing walls of a blood vessel. In this way, the blood vessel can be fused closed, resulting in a sealing of the vessel at the fused region. Surgical instruments that perform this action are often referred to as sealing instruments (e.g., a "vessel sealer"). Such electrosurgical instruments also can be used, for example, for cold-cutting, tissue dissection, coagulation of tissue bundles generally (e.g., other than for sealing), and tissue manipulation/retraction. Once tissues, such as, for example, those of a blood vessel, are fused together, the fused region can be cut without any resulting bleeding.

An end effector of an electrical flux delivery instrument can include a pair of opposing jaw members pivotably coupled together to open and close so as to clamp or otherwise retain a material (e.g. tissues) through which energy will be passed. Accordingly, one of a pair of opposing electrodes provided as part of each of the pair of opposing jaw members, respectively. Generally, the opposing electrodes themselves have a proximal end and a distal end, with proximal generally being in a direction closest to the location where the jaw members are pivotably coupled to each other.

There is a continued need to improve upon spacers used to maintain a distance between opposing electrodes so as to provide robust spacer mechanisms that facilitate manufacturing, are durable, and/or have a configuration that allows for a relatively large exposed area of the electrode surfaces.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, the present disclosure contemplates n electrode assembly comprises an electrode support, an electrode on the electrode support, the electrode having a working surface extending generally transverse to a thickness of the electrode, and a filament of electrically insulative material overlying a portion of the working surface of the electrode and at least partially extending through the thickness of the electrode.

In yet another exemplary embodiment, the present disclosure contemplates an electrosurgical instrument comprising a shaft and an end effector operably coupled to the shaft, the end effector comprising a pair of opposing jaw members, each jaw member comprising an electrode assembly disposed to face the electrode assembly of the opposing jaw member. At least one electrode assembly comprises an electrode support supported by a body of the respective jaw member, an electrode on the electrode support, the electrode having a working surface extending generally transverse to a thickness of the electrode, and a filament of electrically insulative material overlying a portion of the working surface of the electrode and at least partially extending through the thickness of the electrode. The present disclosure further contemplates in an exemplary embodiment a method for making an electrode assembly comprising providing an electrode with a plurality of openings extending at least partially through a thickness of the electrode, overlaying the electrode on an electrode support, supporting the electrode support with a jaw body, stitching a filament made of electrically insulative material comprising a first inset segment and exposed segment into a first opening of the plurality of openings such that the first inset segment is positioned in the first opening and at least a portion of the exposed segment is positioned to overlie an exposed working surface of the electrode, and affixing at least an end portion of the first inset segment of the filament to the electrode, electrode support, and/or the jaw body.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIG. 1 is a diagrammatic perspective view of a minimally invasive surgical instrument in accordance with an exemplary embodiment of the present disclosure.

FIG. 3A is a longitudinal cutaway view of a pair of opposing jaw members of an end effector comprising an electrode assembly in accordance with an exemplary embodiment of the present disclosure.

FIG. 3B is a longitudinal cross-sectional view of the end effector of FIG. 3A with the jaw members in a closed position.

FIG. 3C is a longitudinal cross-sectional view of the end effector of FIG. 3A with the jaw members in an open position.

FIG. 5A is a longitudinal cutaway view of a pair of opposing jaw members of an end effector comprising an electrode assembly in accordance with yet another exemplary embodiment of the present disclosure.

Figure 2A:
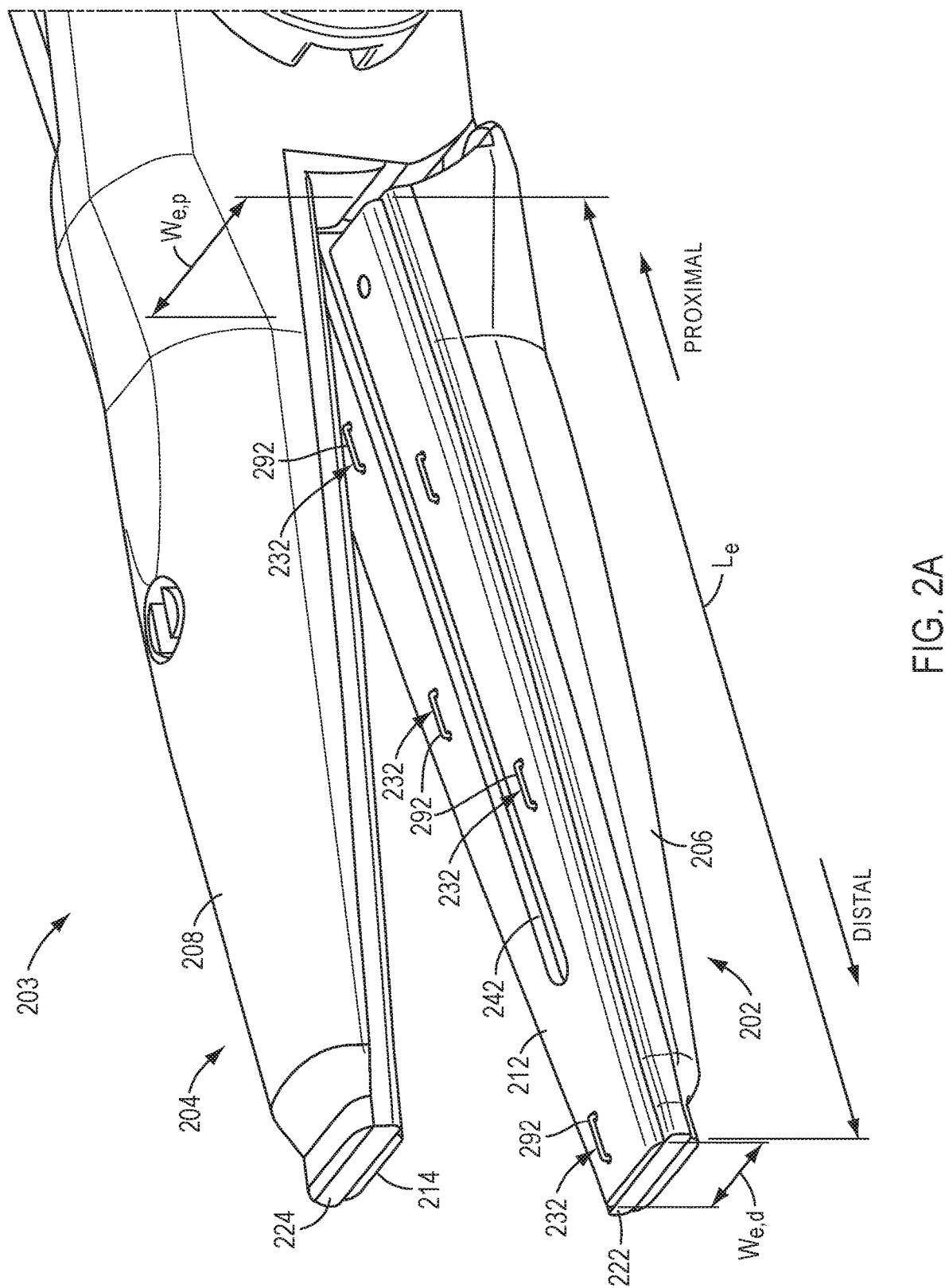
FIG. 2A is a detailed side perspective view of opposing jaw members of an end effector of a surgical instrument in an open position in accordance with an exemplary embodiment.

Although the following detailed description makes reference to exemplary illustrative embodiments, many alternatives, modifications, and variations thereof will be apparent to those skilled in the art and are contemplated as within the scope of the present disclosure and claims. Accordingly, it is intended that the claimed subject matter is provided its full breadth of scope, including encompassing equivalents.

DESCRIPTION OF EXEMPLARY EMBODIMENTS

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the,"

and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

This description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. In the orientation of the figures in the application, relative proximal and distal directions of the devices have been labeled.

The present disclosure contemplates electrode assemblies, and electrical flux delivery instruments including the same, having one or more insulative electrode spacers. In addition, the present disclosure contemplates systems and methods related to electrode assemblies having one or more electrically insulative electrode spacers, as well as electrical flux delivery instruments including the same.

An electrode spacer of an electrode assembly according to various exemplary embodiments is a filament. An electrode spacer filament in accordance with the present disclosure may include one or more fibers or strands. For example, a filament may comprise a fibrous thread made up of a plurality of fibers.

An electrode spacer filament of an electrode assembly according to various exemplary embodiments of the present disclosure includes at least a first inset segment and an exposed segment. The first inset segment of the filament may be stitched into an opening of an electrode of the electrode assembly such that the first inset segment is affixed, restrained, or otherwise positioned in the opening of the electrode, the exposed segment of the electrode spacer can extend beyond the opening, and at least a portion of the exposed segment may lie on the exposed surface of the electrode. Accordingly, when opposing electrodes are brought together to clamp or grip material therebetween, the exposed segment of the filament keeps the electrodes spaced apart by a gap that corresponds to the thickness of the exposed segment of the electrode spacer filament under the load of opposing electrode. Furthermore, electrode spacer filaments according to exemplary embodiments of the present disclosure are made of relatively electrically insulative material(s), which prevents a short circuit and undesirable electrical arcing by impeding (e.g., preventing) the electrode surfaces made of conductive material from being driven into mutual contact and sufficiently spaced from one another.

Electrode assemblies in accordance with various exemplary embodiments of the present disclosure may be designed to be long-lasting and resistant to damage or failure. To provide such durability, at least the exposed segment of each of the insulative electrode spacer filaments of an electrode assembly in accordance with various exemplary embodiments of the present disclosure may be made of relatively high strength material(s) capable of withstanding temperatures of at least about 220° F., such as, for example, one or more aramids or cotton. Exemplary aramids that may be used include, for example, those commercially available under the trade names Kevlar®, Twaron®, Nomex®, and Vectran™.

To make an electrode spacer filament as disclosed herein sufficiently electrically insulative, for example to prevent shorting and arcing as discussed above, various exemplary embodiments contemplate the material(s) of at least the exposed segment of the spacer filament being relatively electrically insulative. In various exemplary embodiments in accordance with the present disclosure, an electrically insulative exposed segment of a filament has a dielectric strength of at least 50 V/mil (i.e., volts per 0.001 inch). In various other exemplary embodiments in accordance with the present disclosure, an insulative exposed portion of a filament has a dielectric strength of at least 150 V/mil or at least 200 V/mil (i.e., volts per 0.001 inch). A person of ordinary skill in the art would understand that the dielectric strength of at least the exposed portion of an electrode spacer filament in accordance with the present disclosure will vary in accordance with the type of instrument in which the electrode spacer is to be incorporated and/or with the magnitude of the voltage of the electrical energy being passed between electrodes.

Regardless of the material of the electrode spacer filament, a person having ordinary skill in the art would understand that, at a minimum, the electrode spacer filament should have a dielectric strength that is greater than the quotient of the voltage to be applied across the electrodes over the thickness of the electrode spacer that spans between the electrodes. For example, if 100 volts are being are to be applied across the electrodes, and the thickness of the electrode spacer filament spanning between the electrodes is 0.010 inches, then the dielectric strength of the spacer filament must be greater than 100 V/0.010 inches, which is equal to 10 V/mil, in order to be an effective electrical insulator.

In various exemplary embodiments, at least the exposed segment of an insulative electrode spacer filament is coated with an electrically insulative coating, such as, for example, silicone, polyphthalamide (PPA), polyether ether ketone (PEEK), epoxy, and/or light cured materials. In some embodiments, for example, where the filament is a fibrous thread, the thread may be coated such that the voids between the plurality of fibers of at least the exposed portion of the thread are impregnated with the coating material(s). Such impregnation can prevent body fluids from soaking into the thread which otherwise could cause undesirable reduction in dielectric strength of the thread and undesirable sticking between opposing electrodes of surgical instrument during use, for example, during performance of electrosurgical procedures. Coating a filament can also increase the durability of the filament by improving a spacer filament's resistance to being snagged or cut during manufacturing of the electrode assembly or by other surgical instruments during use in a medical procedure. A coating material may also serve to bond the filament to an electrode or other components of an electrode assembly.

Electrodes of an electrode assembly in accordance with various exemplary embodiments of the present disclosure are made of conductive materials, such as, for example, metal(s) or metal injection molded material(s), such as, for example, stainless steel, zirconium, titanium, or combinations thereof.

In various exemplary embodiments of an electrode assembly, one or more insulative spacer filaments may be in the form of one or more threads stitched into the thickness of an electrode made of metal. For example, various exemplary embodiments contemplate forming electrode assemblies in accordance with the present disclosure by metal injection molding the electrode with openings in the electrode body, each opening being configured to receive an inset segment of an insulative electrode spacer thread therein and to hold at least a part of the inset segment of the spacer thread in a thickness of the electrode. In other various exemplary embodiments, for example, electrode assemblies in accordance with the present disclosure may include a stamped stainless steel electrode with openings in the body of the electrode, each opening being configured to receive an inset segment of an insulative electrode spacer thread therein and to hold at least a part of the inset segment of the spacer in a thickness of the electrode.

Regardless of the materials of construction, exemplary embodiments of an electrode assembly according to the present disclosure include a plurality of insulative electrode spacer filaments that each have an exposed segment and at least one inset segment that is positioned at least partially in a thickness of the electrode. A first inset segment of the insulative spacer filaments may be positioned extending at least partially into a thickness of an electrode by being stitched into one of a plurality of openings (e.g., through holes, notches, cut outs, slots, depressions) in an electrode such that the exposed segment of the filament extends out of the opening and at least a portion of the exposed segment lies on the exposed surface of the electrode.

In some exemplary embodiments, each of the plurality of the electrically insulative spacer filaments further include a second inset segment with the exposed segment extending between the first inset segment and the second inset segment (i.e., the first inset segment and the second inset segment are separated by the exposed segment). Optionally, the second inset segment may be positioned extending into a thickness of an electrode by, for example, being stitched into another one of the plurality of openings. In particular, it is contemplated that in various exemplary embodiments a first end (comprised by a first inset segment) of each electrically insulative spacer filament is threaded into at least a first opening of a plurality of openings in an electrode, a second end (comprised by a second inset segment) of each filament is threaded into at least a second opening of a plurality of openings in the electrode, an exposed segment of each filament extends between the first and second end of the filament, and at least part of the exposed segment lies on a working surface of the electrode of the electrode assembly.

In some other exemplary embodiments, each of the plurality of the electrically insulative spacer filaments does not include a second inset segment. Rather, an insulative electrode spacer filament can have a single inset segment that is positioned at least partially in a thickness of the electrode via an opening such that the exposed segment of the filament extends out of the opening and at least a portion of the exposed segment lies on the exposed surface of the electrode. According to some of these exemplary embodiments, the exposed segment may be affixed to the exposed surface of the electrode via a knot, and the single inset segment may be affixed below the exposed surface of the electrode via a knot.

In various exemplary embodiments, each of the plurality of openings extend through the entire thickness of the electrode and further into a thickness of the electrode support upon which the electrode lies, thereby allowing the first inset segment to extend through the entire thickness of the electrode and into the electrode support via a first opening, and likewise allowing the second inset segment (if present) to extend through the entire thickness of the electrode and into the electrode support via a second opening. In various exemplary embodiments where first and second inset segments extend through the electrode and into the electrode support, the first and/or second inset segments may be affixed to the electrode support. The first and/or second inset segments of the electrically insulative spacer filament may be affixed to the electrode support via a tie, a knot, an adhesive, a bond, or an overmolded encapsulation. The electrode and the electrode support can be joined by virtue of the first and/or second inset segments being affixed to the electrode support, and such joining may substantially or entirely prevent relative movement between the electrode and the electrode support.

Thus, insulative electrode spacer filaments according to various exemplary embodiments of the present disclosure can not only maintain the desired gap between electrodes, they also can be used to join two or more components of an electrode assembly, such as the electrode and electrode support, for example, by one or more of tying, sewing, stitching, or binding the parts together.

In various other exemplary embodiments, each of the plurality of openings may be a slot or depression that extends partially through the entire thickness of the electrode (e.g., a blind recess). In such embodiments, the first inset segment may extend partially into the thickness of the electrode via a first opening, and likewise the second inset segment (if present) may extend partially into the thickness of the electrode via a second opening. The extent that the first inset segment and second inset segment extend into the thickness of the electrode is defined by the depth of the first opening and second opening, respectively. In such embodiments, the first and/or second inset portions of the electrically insulative spacer filament may be affixed to the electrode via an adhesive, a bond, and/or an overmolded encapsulation.

In still other various exemplary embodiments, each of the plurality of openings may be a notch or indentation formed along a side edge of the electrode that extends through the entire thickness of the electrode. In such embodiments, the first inset segment extends along the thickness of the electrode via a first opening, and likewise the second inset segment extends along the thickness of the electrode via a second opening. In some of these embodiments, the extent that the first inset segment and second inset segment extend along the thickness of the electrode is defined by the depth of the first opening and second opening, respectively. In such embodiments, the first and/or second inset portions of the electrically insulative spacer filament may be affixed to the electrode via an adhesive, a bond, or an overmolded encapsulation. Optionally, the first inset segment and second inset segment extend around and along the entire jaw member such that respective ends of the first inset segment and second inset segment are joined and the filament wraps around the entire jaw member so as to bind the jaw member, with the notched openings retaining the insulative electrode spacer filament in place.

Although discussed herein primarily with respect to surgical instrument applications, the present disclosure contemplates that the various electrode spacers and electrode assemblies disclosed herein may be suitable for other applications that utilize opposing electrode assemblies to deliver electrical flux. Accordingly, the present disclosure is not intended to be limited to surgical instruments or applications.

With reference now to FIG. 1, a perspective view of a minimally invasive surgical instrument 10 is illustrated. The directions "proximal" and "distal" are used herein to define the directions as shown in FIG. 1, with distal generally being in a direction further along a kinematic arm or closest to the surgical work site in the intended operational use of the instrument 10, for example, in use for performing surgical procedures. As shown in FIG. 1, the instrument 10 generally includes a force/torque drive transmission mechanism 1, an instrument shaft 2 mounted to the transmission mechanism 1, an end effector 3 disposed at the distal end of the instrument 10, and an optional articulation wrist 4 disposed at a distal end of the shaft 2 to support the end effector 3 on the shaft 2.

Figure 6:
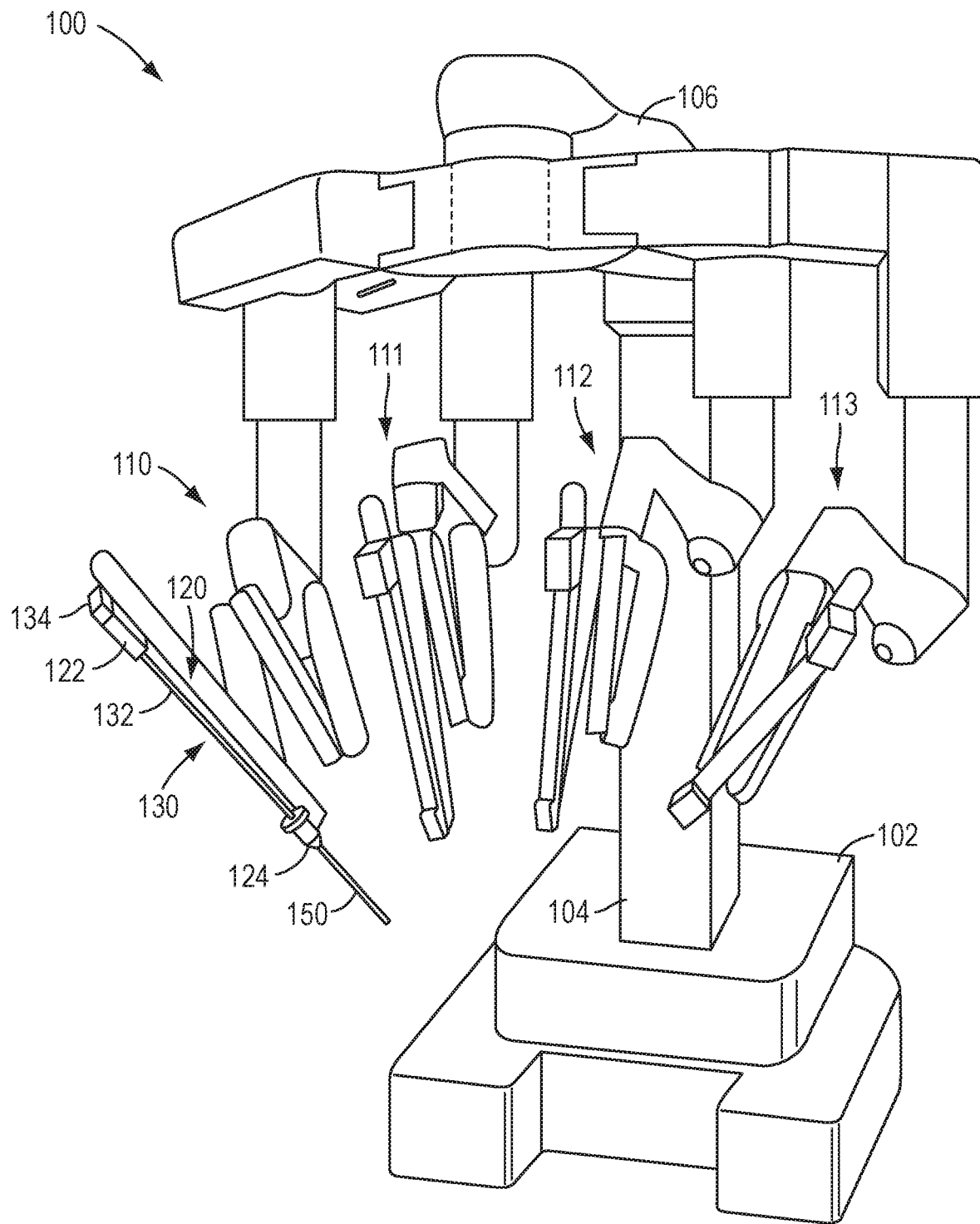
FIG. 6 is a perspective diagrammatic view of a patient side cart in accordance with an exemplary embodiment.

As discussed above, in accordance with various exemplary embodiments, surgical instruments of the present disclosure are configured for use in teleoperated, computer-assisted surgical systems (sometimes referred to as robotic surgical systems). Referring now to FIG. 6, an exemplary embodiment of a patient side cart 100 of a teleoperated, computer-assisted surgical system, to which surgical instruments are configured to be mounted for use, is shown. Such a surgical system may further include a surgeon console (not shown) for receiving input from a user to control instruments of patient side cart 100, as well as an auxiliary control/vision cart (not shown), as described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. Non-limiting, exemplary embodiments of teleoperated, computer-assisted surgical systems with which the principles of the present disclosure may be utilized include the da Vinci® Si Surgical System, Single Site da Vinci® Surgical System, or a da Vinci® Xi Surgical System, available from Intuitive Surgical, Inc. of Sunnyvale, Calif.

Patient side cart 100 includes a base 102, a main column 104, and a main boom 106 connected to main column 104. Patient side cart 100 also includes a plurality of jointed set-up arms 110, 111, 112, 113, which are each connected to main boom 106. Arms 110, 111, 112, 113 each include an instrument mount portion 120 to which an instrument may be mounted, such as instrument 130, which is illustrated as being attached to arm 110. Arms 110, 111, 112, 113 include manipulator portions that can be manipulated during a surgical procedure according to commands provided by a user at the surgeon console. In an exemplary embodiment, signal(s) or input(s) transmitted from a surgeon console are transmitted to the control/vision cart, which interprets the input(s) and generate command(s) or output(s) to be transmitted to the patient side cart 100 to cause manipulation of an instrument 130 (only one such instrument being mounted in FIG. 1) and/or portions of arm 110 to which the instrument 10 is coupled at the patient side cart 100. Those having ordinary skill in the art would understand that the processor/controller functionality need not be included in an auxiliary/vision cart separate from the patient side cart and surgeon console, but rather could be on a different piece of equipment, on the surgeon console or patient side cart, or distributed between those components.

Instrument mount portion 120 comprises an actuation interface assembly 122 and a cannula mount 124, with a force transmission mechanism 134 of instrument connecting with the actuation interface assembly 122. Cannula mount 124 is configured to hold a cannula 150 through which shaft 132 of instrument 130 may extend to a surgery site during a surgical procedure. Actuation interface assembly 122 contains a variety of drive and other mechanisms that are controlled to respond to input commands at the surgeon console and transmit forces to the force transmission mechanism 134 to actuate instrument 10, as those skilled in the art are familiar with.

Although the exemplary embodiment of FIG. 6 shows an instrument 120 attached to only arm 110 for ease of viewing, an instrument may be attached to any and each of arms 110, 111, 112, 113. An instrument 120 may be a surgical instrument with an end effector, such as instrument 10 as discussed above with reference to FIG. 1. A surgical instrument with an end effector may be attached to and used with any of arms 110, 111, 112, 113. However, the embodiments described herein are not limited to the exemplary embodiment of FIG. 6 and various other teleoperated, computer-assisted surgical system configurations may be used with the exemplary embodiments described herein.

Referring again to FIG. 1, the transmission mechanism 1 transmits received actuation inputs, for example, from a patient side cart in computer-assisted surgical systems or manually, to resulting torques and forces to effect movement of the instrument shaft 2, wrist 4, end effector 3, and/or associated components, to accomplish various motions, potentially resulting in a multiple-degrees-of-freedom (multi-DOF) actuation of the surgical instrument. For example, the transmission mechanism 1 can be controlled via inputs (e.g., torque inputs) to roll shaft 2, and consequently end effector 3 (roll DOF); open and close jaws of the end effector 3 (grip or clamp DOF); articulate wrist 4 (articulation DOF); and translate a cutting element (not shown in the view of FIG. 1) (translation DOF), among others. In various exemplary embodiments, the wrist 4 can be configured for two-DOF articulation in orthogonal directions to provide both "pitch" and "yaw" movement of end effector 3 (yaw being arbitrarily defined as being the plane of motion of the end effector jaws, pitch being orthogonal to yaw).

The transmission mechanism 1 also can accommodate electrical conductors (not shown in FIG. 1) to receive electrosurgical energy via connector 42 that is electrically coupled to an electrical flux generation source (not shown but with which those having ordinary skill in the art have familiarity), that is ultimately transmitted to the end effector 3 and used to deliver an electrosurgical flux, for example to fuse or cauterize tissue. The electrical conductors can be routed from the transmission mechanism 1, down the instrument shaft 2 to the end effector 3.

Additional details regarding exemplary, but non-limiting, embodiments of electrosurgical instruments that include a transmission mechanism and a jawed end effector with opposing electrode assemblies configured for performing fusing and cauterizing (e.g., vessel sealing) are disclosed in U.S. Pat. No. 9,055,961 B2, and being titled "FUSING AND CUTTING SURGICAL INSTRUMENT AND RELATED METHODS," and issued Jun. 16, 2015, which is hereby incorporated by reference herein in its entirety.

Figure 2B:
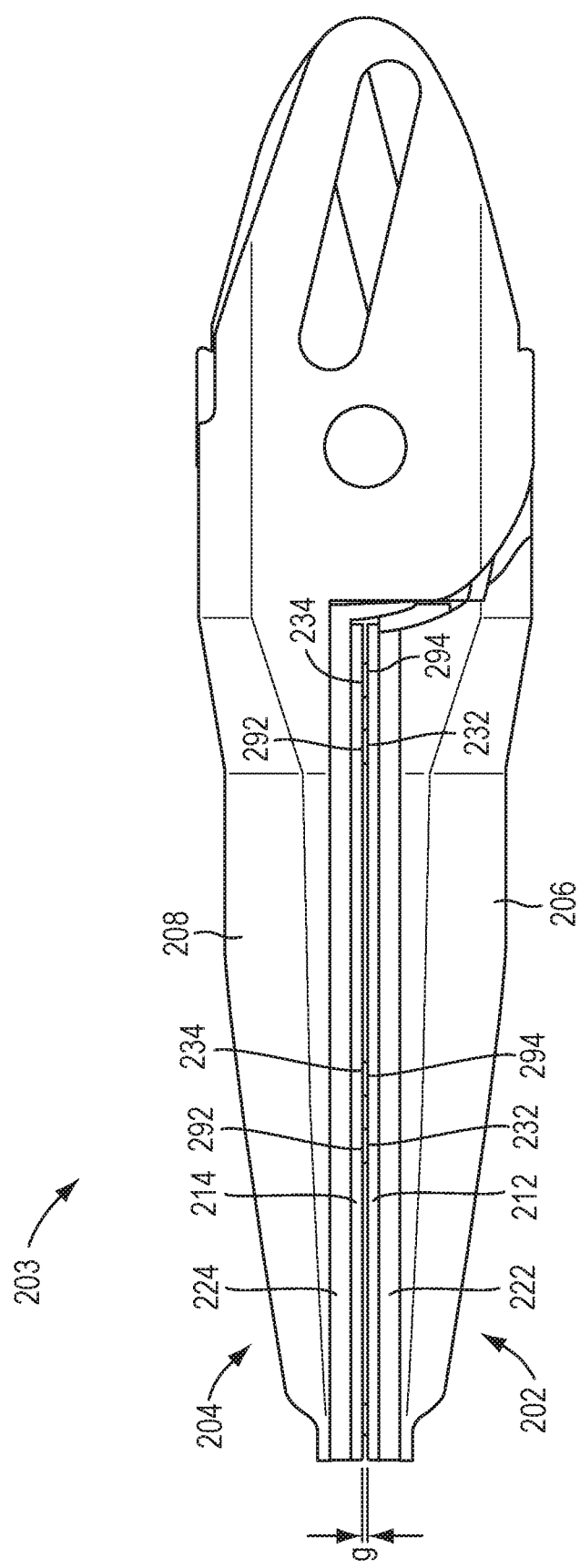
FIG. 2B is a detailed side view of the opposing jaw members of the end effector of FIG. 2A in a closed position.

Turning now to FIGS. 2A and 2B, a detailed side perspective view of an end effector 203 of a surgical instrument, such as, for example the surgical instrument of FIG. 1, is shown. FIG. 2A shows the end effector in an open position and FIG. 2B shows the end effector in a closed position. As shown, the end effector 203 comprises a pair of pivotably coupled opposing jaw members 202, 204. The jaw members 202, 204 extend generally longitudinally and distally from the surgical instrument shaft (not shown in FIG. 2A). At their proximal ends, the jaw members are coupled together to pivot relative to each other between an open position (FIG. 2A) and a closed position (FIG. 2B). The first jaw member 202 includes first jaw body 206 and supports a first electrode assembly including a first electrode 212, a first electrode support 222, and a first plurality of electrode spacers 232. The second jaw member 204 includes second jaw body 208 and supports a second electrode assembly including a second electrode 214, a second electrode support 224, and a second plurality of electrode spacers 234 (hidden from view in FIG. 2A).

The length, $L_e$, of each of the electrodes 212, 214 in various exemplary embodiments may range, for example, from about 6 mm to about 40 mm, or from about 16 mm to about 19 mm, which may be desirable for sealing a vessel having a diameter from about 0.1 mm to about 10 mm, or of about 7 mm, although other lengths and diameters may be used depending on the desired application. The width of the electrodes 212, 214, as well as the corresponding jaws members 202, 204, can present a generally tapered shape, for example, having a larger width at the proximal end and a narrower width at the distal end. Such a tapered shape can be beneficial for dissection of tissue, including dissection of vessels. For example, the tapered shape can improve visibility during dissection and can provide a smaller contact area to pierce tissue. In various exemplary embodiments, the width at the proximal end, $W_{e,p}$, ranges from, for example, about 4 mm to about 12 mm, or in some exemplary embodiments, the width $W_{e,p}$ ranges from about 4 mm to about 8 mm; and the width, $W_{e,d}$, at the distal end ranges from, for example, about 1 mm to about 12 mm, or, for another example, the width $W_{e,d}$ may range from about 1 mm to about 8 mm. Such width ranges are exemplary only and more generally the width of the electrodes 212, 214 can be selected based on the desired application, such as, for example, to provide fusing of both sides of dissected tissue (e.g., dissected ends of a vessel) gripped between the jaw members 202, 204. For example, the width may be selected to provide at least about a 1 mm seal on either side of the dissected tissue. The thickness of each electrode 212, 214 in various exemplary embodiments may range from about 0.001 in. to about 0.020 in, or from about 0.005 in. to about 0.015 in., for example, the thickness may be about 0.010 in.

In the exemplary embodiments depicted, such as in FIGS. 2A and 2B, each of the electrodes 212, 214 is provided with a groove 242 (the corresponding groove on electrode 214 is hidden from view in FIG. 2A) configured to receive and provide a track for a cutting blade that translates in the proximal and distal directions relative to the jaw members 202, 204. However, in instruments that do not include such a cutting element, the groove in the electrode may be omitted.

As shown in FIG. 2A, one or more electrode spacers in the form of filaments, for example, threads, may be provided on the working surface of one or both of the electrodes 212, 214. With reference to FIG. 2B, in the closed position of the jaw members 202, 204, electrode spacer filaments 232, 234 are provided on both of the electrodes 212, 214 to maintain the electrodes 212, 214 spaced apart by a gap g. In various exemplary embodiments, the size of the gap g may range from 0.0005 inches to about 0.008 inches, or the size of gap g may range from about 0.001 inches to about 0.007 inches.

The insulative electrode spacer filaments 232, 234 are disposed at intervals (which can be uniform or random) along the longitudinal length of each jaw member 202, 204, respectively. Also, insulative electrode spacer filaments 232, 234 may be staggered on top and bottom jaws so that filaments 232 make contact with the surface of electrode 214 and filaments 234 make contact with the surface of electrode 212 surface in the closed position of the jaw members 202, 204, rather than spacer filaments 232, 234 making contact with each other.

Figure 7:
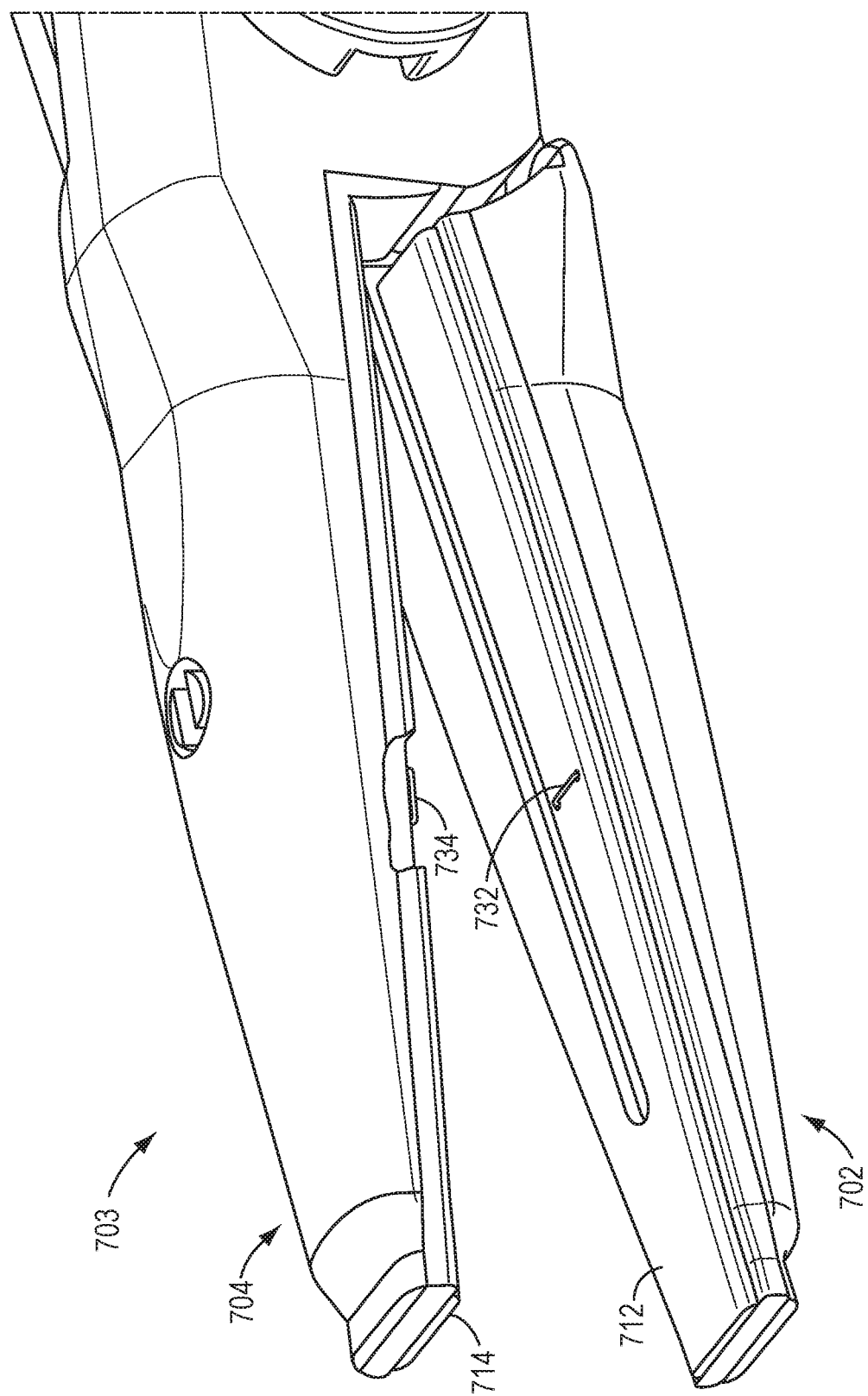
FIG. 7 is a perspective view of a pair of opposing jaw members of an end effector comprising an electrode assembly in accordance with another exemplary embodiment of the present disclosure, the upper jaw member being partially cutaway.

Alternatively, with reference now to the exemplary end effector 703 shown in FIG. 7, insulative electrode spacer filaments 732, 734 may be aligned on top and bottom jaw members 702, 704, respectively, so that spacer filaments of the top jaw electrode assembly make contact with spacer filaments of the bottom jaw electrode assembly in the closed position of the jaw members 702, 704. In order to ensure contact between aligned insulative electrode spacer filaments of opposing electrode assemblies, opposing spacer filaments 732, 734 may be oriented along exposed surfaces of electrodes 712, 714, respectively, such that the longitudinal orientations of opposing spacer filaments cross one another when the jaw members 702, 704 are closed. For example, in the exemplary embodiment shown in FIG. 7, spacer filament 734 on first electrode 714 is longitudinally oriented such that it is substantially parallel to the length $L_e$ of each of the electrodes and an opposing spacer filament 732 on an opposing electrode 712 is longitudinally oriented substantially perpendicular to the length $L_e$ of each of the electrodes 712, 714. Those having ordinary skill in the art would appreciate other respective orientations of aligned spacer filaments that permit the filaments to cross each other.

Referring again to FIGS. 2A and 2B, in an exemplary embodiment, the thickness of the electrode spacer filaments 232, 234 on the exposed surface of the electrodes 212, 214 at the proximal portion of the jaw members 202, 204 may be slightly lower than the thickness of the electrode spacers 232, 234 on the exposed electrode surfaces at the distal portion of the jaw members 202, 204 to promote a uniform gap g across the length of the electrode surfaces while also permitting the electrode surfaces to come sufficiently close along their entire length to ensure effective gripping and sealing of tissue.

In various exemplary embodiments, the exposed segments 292, 294 of insulative electrode spacer filaments 232, 234 have a thickness when the jaw members 202 and 204 are in the closed position (see FIG. 2B) that generally corresponds to the desired gap distance between the electrodes 212, 214. For example, the thickness of the exposed segment of each electrode spacer filaments on the exposed surface of the electrodes ranges from about 0.0005 inches to about 0.008 inches, or from about 0.001 inches to about 0.007 inches, when the jaw members are in the closed position. In some embodiments, the nominal thickness of the of the exposed segment of each electrode spacer filaments may not be the same as the thickness that results when the jaw members are closed and imparting a load onto the exposed segment of each of the electrode spacer filaments.

Advantageously, an exposed segment 292, 294 of each electrode spacer filament 232, 234 may have a small surface profile relative to the surface profile of the exposed surface of the electrode 212, 214. For example, in some exemplary embodiments, the exposed segment 292, 294 of each electrode spacer filament 232, 234 may have a working surface area of about 0.3 mm$^2$ ($5 \times 10^{-5}$ in.$^2$). Accordingly, the ratio of the working surface area of the exposed portions 292, 294 of each electrode spacer filament 232, 234 to the area of the exposed surface of each electrode may range from about 0.002 to about 0.08.

By disposing the electrode spacer filaments 232, 234 at intervals along the longitudinal length of each jaw member 202, 204, respectively, and/or providing electrode spacer filaments 232, 234 with exposed segments 292, 294 having a relatively small laterally extending working profile, as described herein, sealing and/or cauterizing can occur over substantially the entire surfaces of the full length of the electrode assemblies.

In addition to maintaining electrodes spaced apart by a gap g, the electrode spacer filaments 232, 234 may also improve the grasping capability of the end effector 203. In various exemplary embodiments, an electrode assembly may include additional electrode spacers beyond what would be required to maintain a gap in order to enhance the grasping ability of an end effector.

Figure 3D:
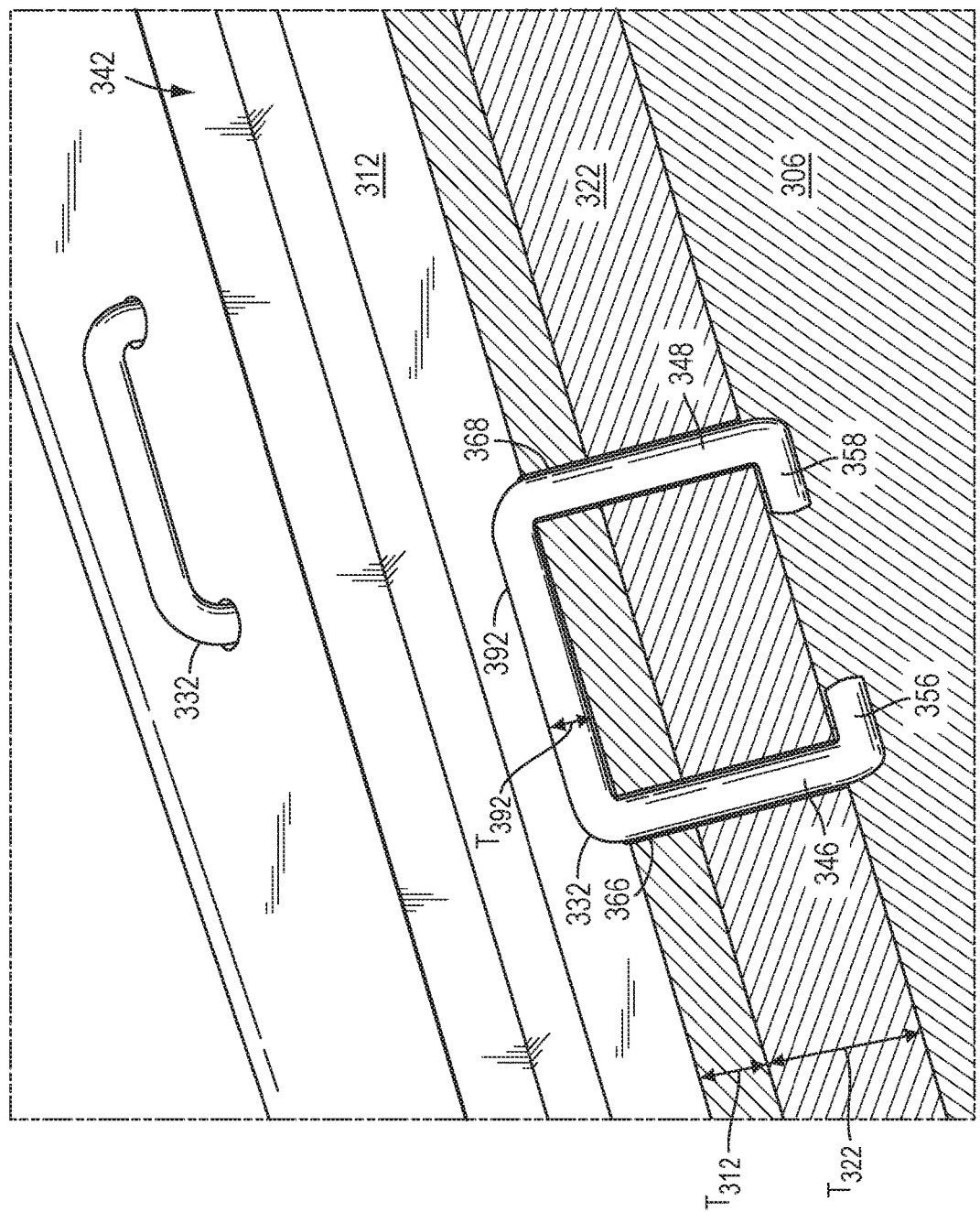
FIG. 3D is a detailed view of the portion labeled FIG. 3D in FIG. 3A.

Turning now to FIGS. 3A-3D, various views of an end effector 303 in accordance with an exemplary embodiment are shown. FIG. 3A shows a perspective longitudinal cut-away view of the end effector 303. FIG. 3B is a longitudinal cross-sectional view of the end effector 303 with the jaw members in a closed position, and FIG. 3C is a longitudinal cross-sectional view of the end effector 303 with the jaw members in an open position. As discussed above with reference to FIGS. 2A and 2B, in the closed position of the jaw members 302, 304, electrode spacer filaments 332, 334 are provided to maintain the electrodes 312, 314 spaced apart by a gap g. In various exemplary embodiments, the size of the gap g may range from 0.0005 inches to about 0.008 inches, or the size of gap g may range from about 0.001 inches to about 0.007 inches. The electrode spacer filaments 332, 334 are disposed at intervals along the longitudinal length of each jaw member 302, 304, respectively. In an exemplary embodiment, the thickness of the electrode spacer filaments 332, 334 on the exposed surface of the electrodes 312, 314 at the proximal portion of the jaw members 302, 304 may be slightly lower than the thickness of the electrode spacer filaments 332, 334 on the exposed electrode surfaces at the distal portion of the jaw members 302, 304 to promote a uniform gap g across the length of the electrode surfaces while also permitting the electrode surfaces come sufficiently close along their entire length to ensure effective gripping and sealing of tissue.

Details of an individual insulative electrode spacer filament 332 can be best seen in FIG. 3D, which is a detailed view of the portion of the jaw member 302 labeled FIG. 3D in FIG. 3A. For simplification and ease of description, the configuration of spacer filaments 332, jaw body 306, electrode 312, and electrode support 322 of an electrode assembly shown in FIG. 3D is discussed and referred to herein, but one having ordinary skill in the art would appreciate the description applies to the opposing spacer filaments 334, electrode 314, and electrode support 324 of an opposing electrode assembly. Each electrode spacer 332 comprises an exposed segment 392 that at least partially overlies the working surface of the electrode 312, and an inset portion, that can comprise, for example, a single segment or two inset segments 346, 348 separated by the exposed segment 392. As shown in FIG. 3D, the exposed segment 392 extends between the first inset segment 346 and second inset segment 348. The electrode 312 and electrode support 322 have a plurality of openings configured to receive and stitch an insulative electrode spacer filament 332. The plurality of openings can include a first opening 366 and a second opening 368.

The first inset segment 346 can be retained in an entire thickness $T_{312}$ of the electrode 312 and in an entire thickness $T_{322}$ of the electrode support 322. The first inset segment end 356 and second inset segment end 358 can each extend into the jaw body 306 and be retained therein via a bond and/or adhesive. Although not shown, the first and second inset segment ends may be additionally or solely affixed to electrode support 322 and/or the jaw body 306 via a tie, knot, and/or an encapsulation that results from overmolding. Additionally, although not shown, it also is contemplated that rather than extending into jaw body 306, the first inset segment end 356 and/or second inset segment end 358 may be retained in the thickness $T_{322}$ of the electrode support 322. The electrode 312 and the electrode support 322 can be joined by virtue of the first and second inset segments 346, 348 being affixed to or otherwise retained in the electrode support 322, and such joining may substantially or entirely prevent relative movement between the electrode 312 and the electrode support 322. Accordingly, as discussed above, spacer filaments 332, 324 can not only maintain the desired gap between electrodes 312, 314, they can also join the electrode 312 and electrode support 322 of an electrode assembly to each other.

As discussed above, the exposed segments 392, 394 of insulative electrode spacer filaments 332, 334 have a thickness when the jaw members 302 and 304 are in the closed position that generally corresponds to the desired gap distance between the electrodes 312, 314. For example, the exposed segment 392 can have a thickness $T_{392}$ ranging from about 0.0005 inches to about 0.008 inches, or the thickness $T_{392}$ may range from about 0.001 inches to about 0.007 inches, when the jaw members 302 and 304 are in the closed position. In some embodiments, the nominal thickness of the of the exposed segment of each electrode spacer filaments may not be the same as the thickness that results when the jaw members are closed and imparting a load onto the exposed segment of the electrode spacer filaments.

As discussed above, in various exemplary embodiments in accordance with the present disclosure, at least the exposed portion 392 of an electrode spacer filament in the form of one or more threads may have a dielectric strength of at least 50 V/mil (i.e., volts per 0.001 inch). In various other exemplary embodiments in accordance with the present disclosure at least the exposed portion 392 of an electrode spacer 332 or 334 may have a dielectric strength of at least 50 V/mil, 150 V/mil, or at least 200 V/mil (i.e., volts per 0.001 inch).

As discussed above, the insulative electrode spacer filaments 332 may be a thread, as best seen in FIG. 3D. The thread may include a plurality of fibers. Alternatively, the thread may include a single fiber strand. Some or all the fiber(s) that make up at least the exposed portion of the thread may be made of relatively high strength material(s) capable of withstanding temperatures of at least about 220° F., such as, for example, one or more aramids or cotton. Exemplary aramids for use in the fiber(s) of a thread include, for example, Kevlar®, Twaron®, Nomex®, and Vectran™.

Furthermore, in some exemplary embodiments, at least the exposed segment 392 of the thread forming the electrode spacer 332 is coated with an electrically insulative coating, such as, for example, silicone. In some embodiments, the spacer thread 332 may be coated such that the voids between fibers of at least the exposed segment 392 of the thread are impregnated with the coating material. Such impregnation can prevent body fluids from soaking into the fibers of the spacer threads and causing undesirable sticking between opposing electrodes of surgical instrument during surgery.

As demonstrated in FIGS. 3A-3D, the electrode support (e.g., electrode support 322, 324) is separate from the insulative electrode spacer filaments (e.g., 332, 334) thereby allowing for the spacers and electrode supports to be made from different materials without increasing the complexity of manufacturing the electrode assembly. Making the electrode support from a different material than the material that the insulative electrode spacer filaments are made can enable the electrode support to be made from a less durable material than the spacer in view of the positioning, configuration, and use of the electrode support not being as prone to damage. The ability to make the support out of a less durable material can in turn reduce overall manufacturing costs of electrode assemblies. Accordingly, in various exemplary embodiments, the electrode supports are made of relatively lower strength insulative material such as, for example, plastic and ceramic.

Figure 4A:
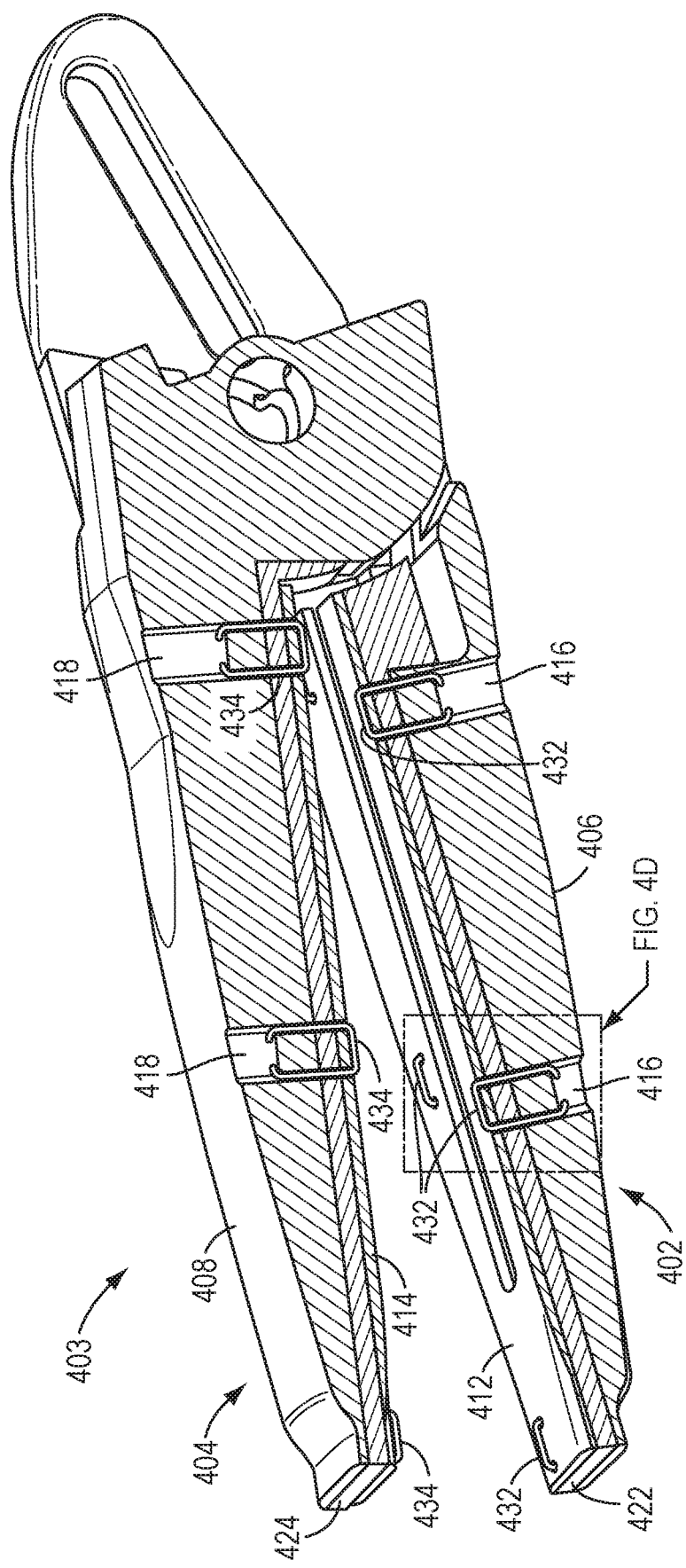
FIG. 4A is a longitudinal cutaway view of a pair of opposing jaw members of an end effector comprising an electrode assembly in accordance with another exemplary embodiment of the present disclosure.
Figure 4B:
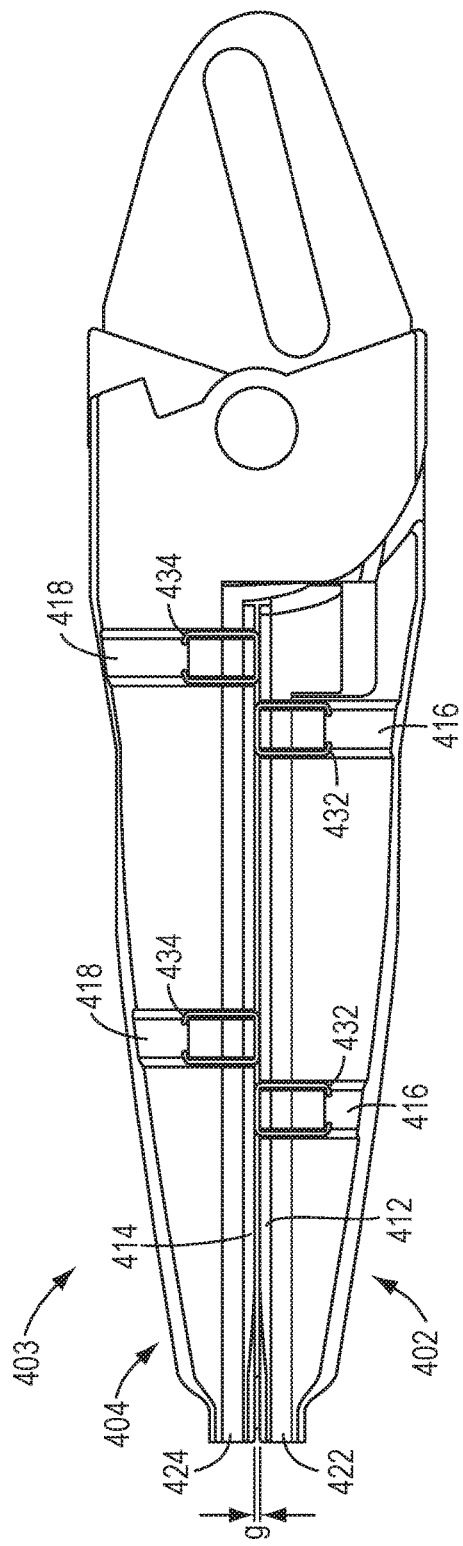
FIG. 4B is a longitudinal cross-sectional view of the end effector of FIG. 4A with the jaw members in a closed position.
Figure 4C:
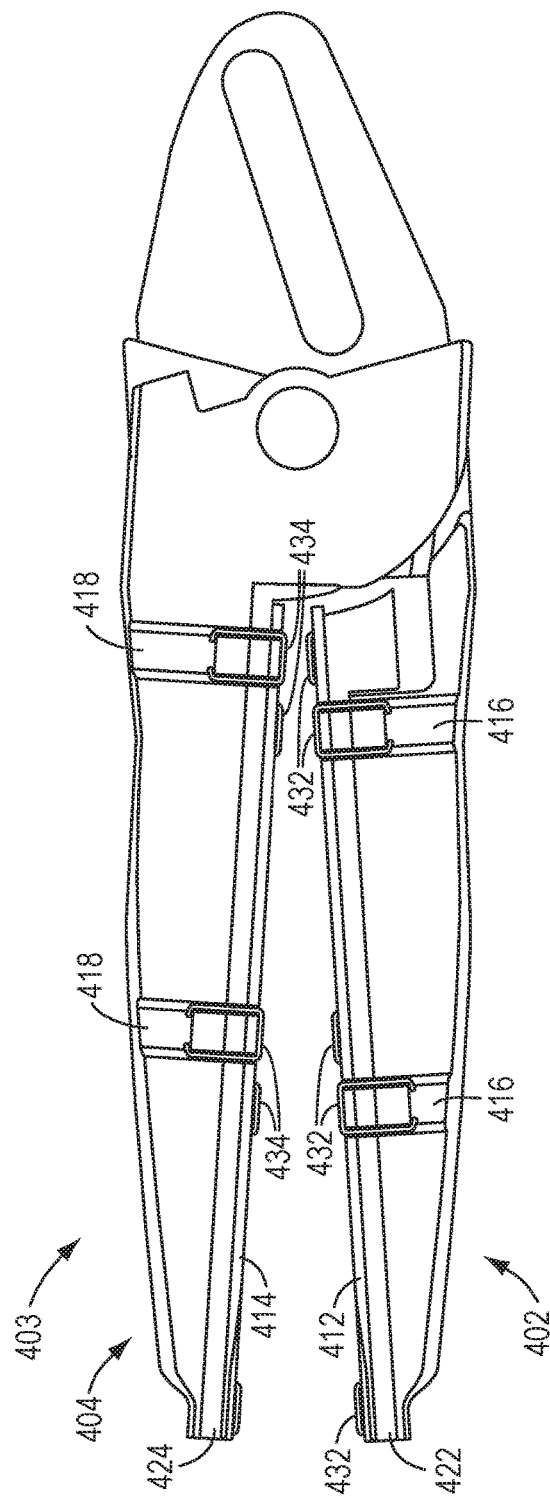
FIG. 4C is a longitudinal cross-sectional view of the end effector of FIG. 4A with the jaw members in an open position.

Turning now to FIGS. 4A-4D various views of an end effector 403 in accordance with an exemplary embodiment are shown. FIG. 4A shows a perspective longitudinal cut-away view of the end effector 403. FIG. 4B is a longitudinal cross-sectional view of the end effector 403 with the jaw members 402, 404 in a closed position, and FIG. 4C is a longitudinal cross-sectional view of the end effector 403 with the jaw members 402, 404 in an open position.

As with the exemplary embodiments of FIGS. 2A-2B and 3A-3D, in the closed position of the jaw members 402, 404, the electrodes 412, 414 of FIGS. 4A-4D are maintained spaced apart by a gap g using electrode spacer filaments 432, 434 disposed at intervals (which can be uniform or random) along the longitudinal length of each jaw member 402, 404, respectively. In various exemplary embodiments, the size of the gap g ranges from about 0.0005 inches to about 0.008 inches, or from about 0.001 inches to about 0.007 inches. Also, in various exemplary embodiments, the height of the electrode spacers above the exposed surface of the electrodes ranges from about 0.0005 inches to about 0.008 inches, or from about 0.001 inches to about 0.007 inches.

Figure 4D:
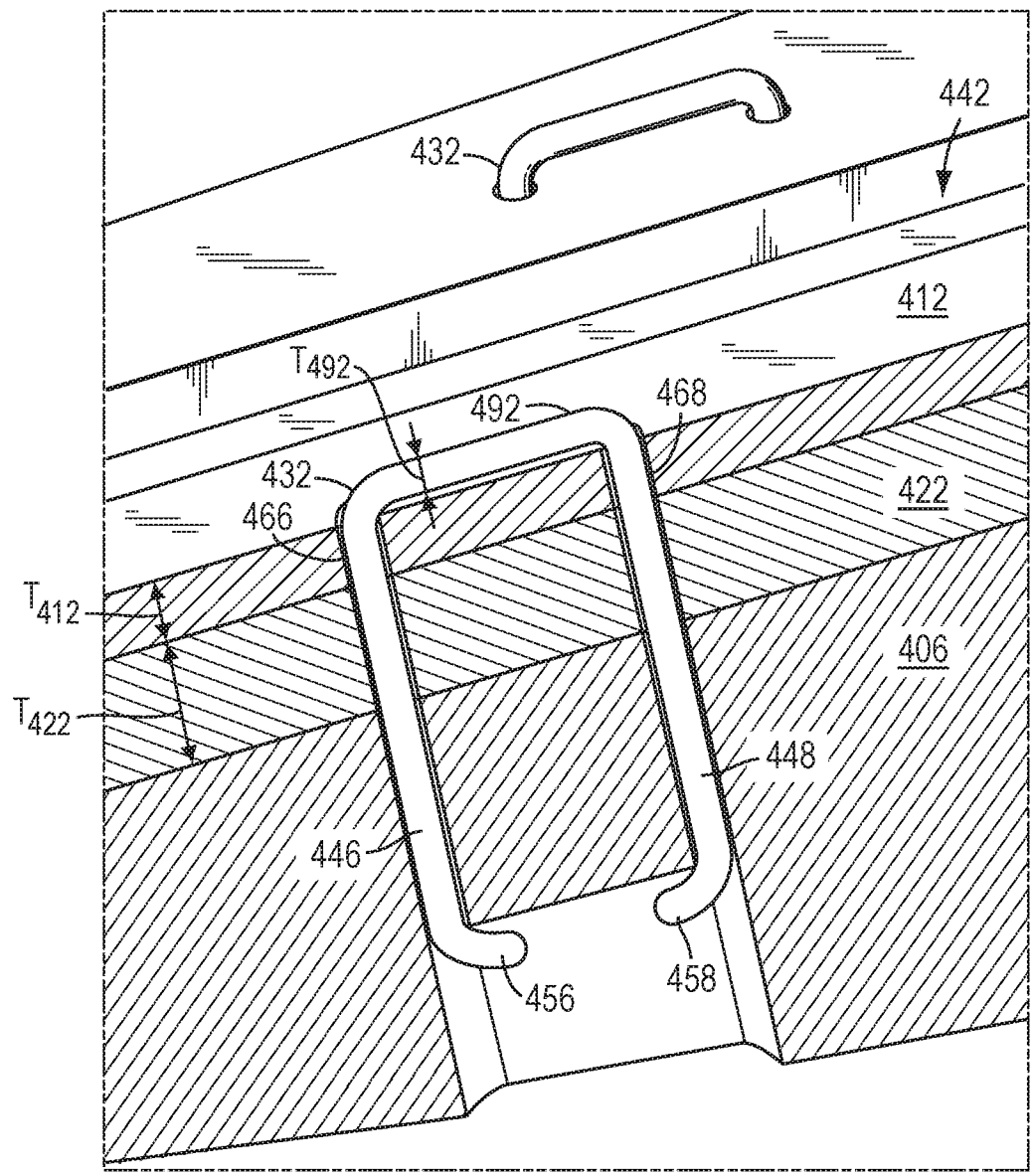
FIG. 4D is a detailed side view of the portion labeled FIG. 4D in FIG. 4A.

As can be best seen in FIG. 4D, which is a detailed side view of the portion labeled FIG. 4D of the jaw member 402, each electrode spacer filament 432, 434 comprises an exposed portion 492 that at least partially overlies the working surface of the electrode 412, a first inset segment 446, and a second inset segment 448. As shown in FIG. 4D, the exposed segment 492 extends between the first inset segment 446 and second inset segment 448. The electrode 412 and electrode support 422 can have a plurality of openings configured to receive an insulative electrode spacer filament 432. The plurality of openings can include a first opening 466 and a second opening 468.

The first inset segment 446 can be stitched such that it is retained in an entire thickness $T_{412}$ of the electrode 412 and in an entire thickness $T_{422}$ of the electrode support 422. The end 456 and 458 of the first inset segment 446 and second inset segment 448, respectively, can each extend into the jaw body 406 and be retained therein via a bond and/or adhesive. Although not shown, the first and second inset segment ends 456, 458 may be additionally or solely affixed to the jaw body 406 via a tie, knot, and/or an encapsulation that results from overmolding. Additionally, as best shown in FIG. 4D, jaw body 406 may have a recess 416 that is open such that the first and second inset segment ends 456, 458 are accessible without having to disassemble the jaw body 406 from the components of the electrode assembly. Likewise, jaw body 408 can have recesses 418 that are open such that first and second inset segment ends of electrode spacer threads 434 are similarly accessible (see FIGS. 4A-4C). Such accessibility can facilitate tying the end(s) of the inset segments and/or applying adhesive to the inset segment ends.

The electrode 412 and the electrode support 422 can be joined by virtue of the first and second inset segments 446, 448 being affixed to or otherwise retained in the electrode support 422 and/or the jaw body 406, and such joining may substantially or entirely prevent relative movement between the electrode 412 and the electrode support 422. Accordingly, as discussed above, spacer filaments 432, 424 can not only maintain the desired gap between electrodes 412, 414, they can also join the electrode 412 and electrode support 422 of an electrode assembly to each other.

Any of the thicknesses, dielectric strengths, thread formations, thread materials, and coating materials discussed above with respect to the exposed segments 392, 394, or the electrode spacer filaments 332, 334, of the end effector 303 shown in FIGS. 3A-3D, may also be applied to the exposed segments 492, 494, or electrode spacer filaments 432, 424, of the end effector 403 shown in FIGS. 4A-4D Accordingly, discussion of the details of the thicknesses, dielectric strengths, thread formations, thread materials, and coating materials of the spacers 432, 424 has been omitted to avoid redundancy.

Figure 5B:
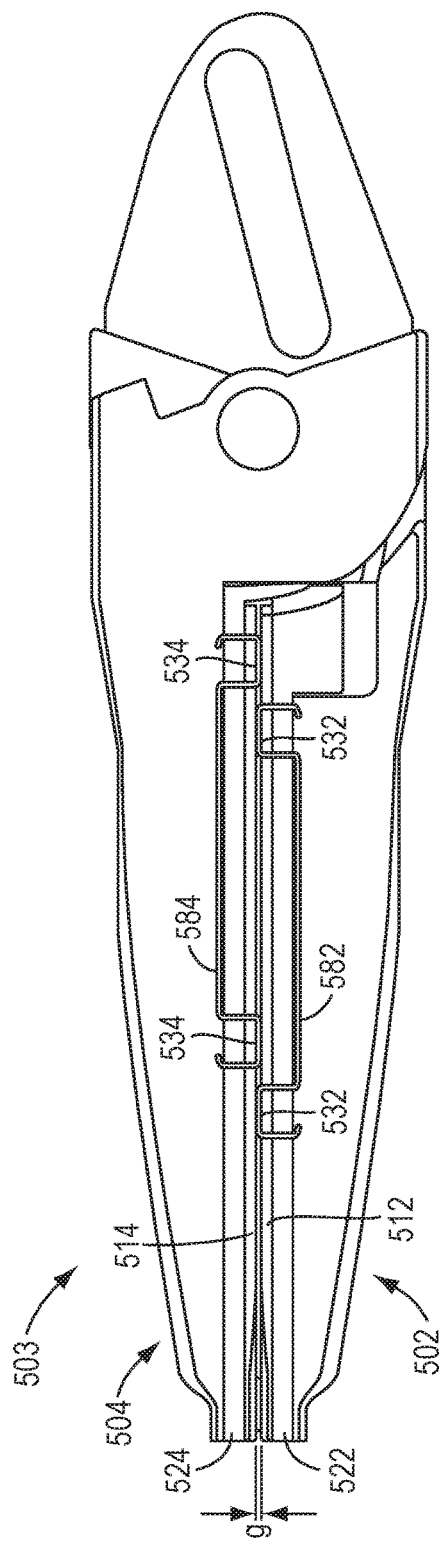
FIG. 5B is a longitudinal cross-sectional view of the end effector of FIG. 5A with the jaw members in a closed position.
Figure 5C:
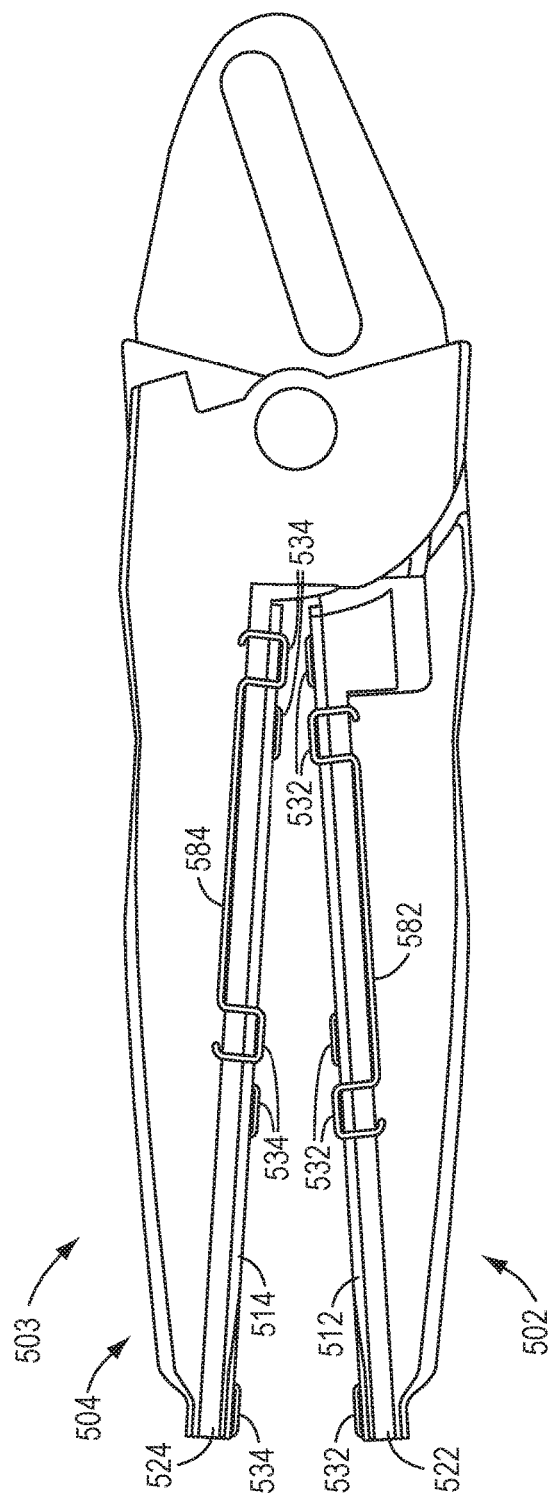
FIG. 5C is a longitudinal cross-sectional view of the end effector of FIG. 5A with the jaw members in an open position.

Turning now to FIGS. 5A-5D various views of an end effector 503 in accordance with an exemplary embodiment are shown. FIG. 5A shows a perspective longitudinal cut-away view of the end effector 503. FIG. 5B is a longitudinal cross-sectional view of the end effector 503 with the jaw members 502, 504 in a closed position, and FIG. 5C is a longitudinal cross-sectional view of the end effector 503 with the jaw members 502, 504 in an open position.

As with the exemplary embodiments of FIGS. 2A-2B, 3A-3D, and 4A-4D, in the closed position of the jaw members 502, 504, the electrodes 512, 514 of FIGS. 5A-5D are maintained spaced apart by a gap g using electrode spacer filaments 532, 534 in the form of thread disposed at intervals (which can be uniform or random) along the longitudinal length of each jaw member 502, 504, respectively. In various exemplary embodiments, the size of the gap g ranges from about 0.0005 inches to about 0.008 inches, or from about 0.001 inches to about 0.007 inches. Also, in various exemplary embodiments, the height of the electrode spacers above the exposed surface of the electrodes may range from about 0.0005 inches to about 0.008 inches, or from about 0.001 inches to about 0.007 inches.

Figure 5D:
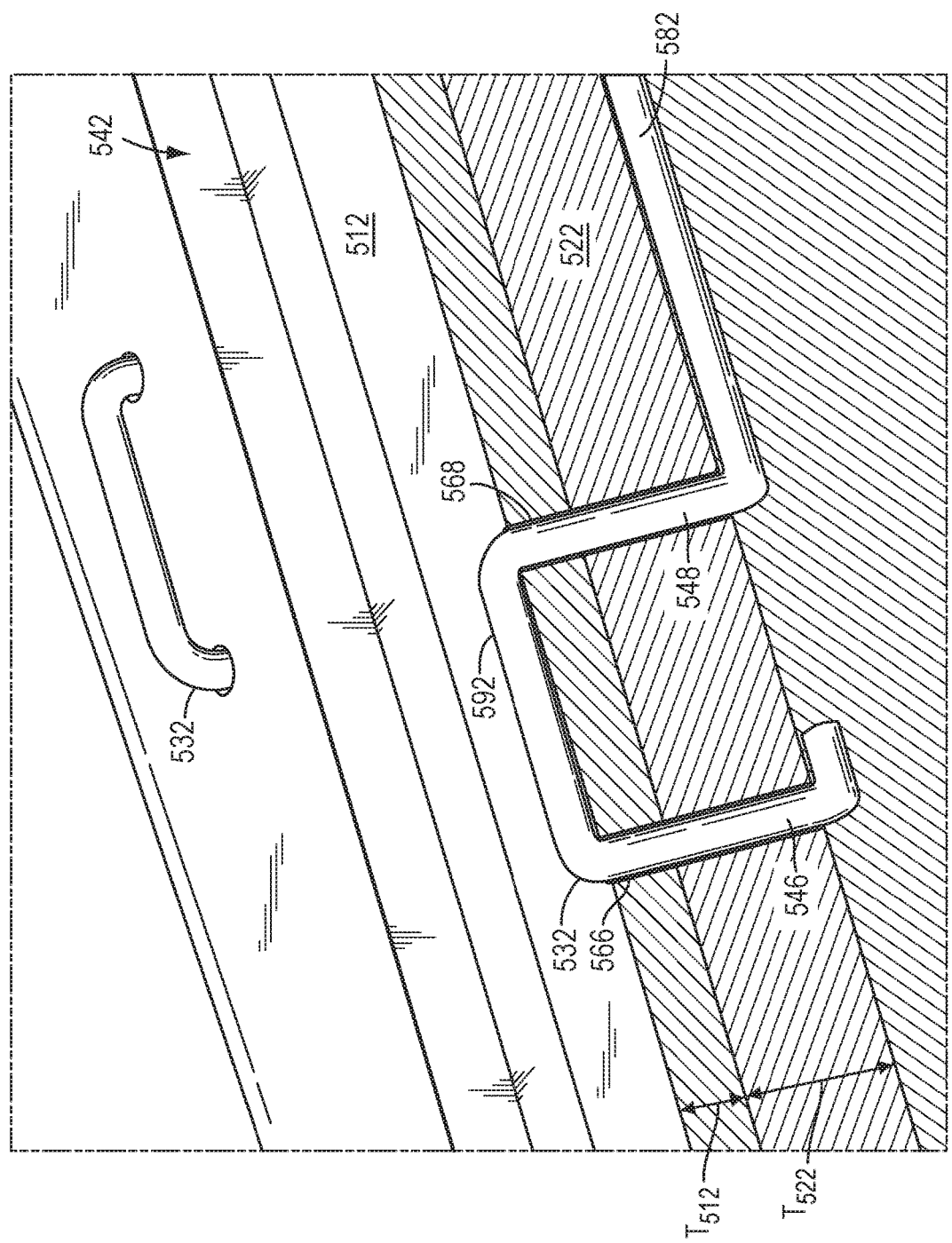
FIG. 5D is a detailed side view of the portion labeled FIG. 5D in FIG. 5A.

As can be best seen in FIG. 5D, which is a detailed side view of the portion labeled FIG. 5D in FIG. 5A of the jaw member 502, each electrode spacer filament 532, 534 comprises an exposed segment 592 that at least partially overlies the working surface of the electrode 512, a first inset segment 546, and a second inset segment 548. As shown in FIG. 5D, the exposed segment 592 extends between the first inset segment 546 and second inset segment 548. The electrode 512 and electrode support 522 can have a plurality of openings configured to receive an insulative electrode spacer filament 532 therein. The plurality of openings can include a first opening 566 and a second opening 568 arranged to provide a stitched pattern for the spacer filament.

The first inset segment 546 can be retained in an entire thickness $T_{512}$ of the electrode 512 and in an entire thickness $T_{522}$ of the electrode support 522. The first inset segment end 556 of the first inset segment 546 can extend into the jaw body 406 and be retained therein via a bond and/or adhesive. Although not shown, the first inset segment end 556 may be additionally or solely affixed to the jaw body 506 via a tie and/or an encapsulation that results from overmolding.

As exemplified by the embodiment of FIGS. 5A-5D, a single thread, made up of one or a plurality of fibers, may be used to form a plurality of electrode spacer filaments of an electrode assembly. For example, a single thread is used to form two of the electrode spacer filaments 532 of the electrode assembly of the jaw member 502. With respect to the electrode assembly of jaw member 502, a single thread may have a connecting portion 582 that extends between inset portions of adjacent electrode spacer filaments 532. Likewise, with respect to the electrode assembly of jaw member 504, a single thread may have a connecting portion 584 that extends between inset portions of adjacent electrode spacer filaments 534.

A single thread may be used to form any number of electrode spacer filaments of an electrode assembly, including all of the electrode spacers of an electrode assembly. Using a single thread to form a plurality of spacers can facilitate manufacturing of an electrode assembly according to the present disclosure. Additionally, using a single thread to form a plurality of spacers reduces the total number a filament ends in an electrode assembly and may thereby reduce waste.

The electrode 512 and the electrode support 522 can be joined by virtue of the first inset portion 546, the second inset portion 548, and/or the connecting portion 582 being affixed to or otherwise retained in the electrode support 522 and/or the jaw body 506, and such joining may substantially or entirely prevent relative movement between the electrode 512 and the electrode support 522. Accordingly, as discussed above, spacer filaments 532, 524 simultaneously maintain the desired gap between electrodes 512, 514 and provide means for joining the electrode 512 and electrode support 522 of an electrode assembly to each other.

Any of the thicknesses, dielectric strengths, thread formations, thread materials, and coating materials discussed above with respect to the exposed portions 392, 394, or the electrode spacers 332, 334 in general, of the end effector 303 shown in FIGS. 3A-3D, may also be applied to the exposed portions 592, 594, or electrode spacers 532, 524 in general, of the end effector 503 shown in FIGS. 5A-5D. Accordingly, discussion of the details of the thicknesses, dielectric strengths, thread formations, thread materials, and coating materials of the spacer filaments 532, 534 has been omitted to avoid redundancy.

Figure 8A:
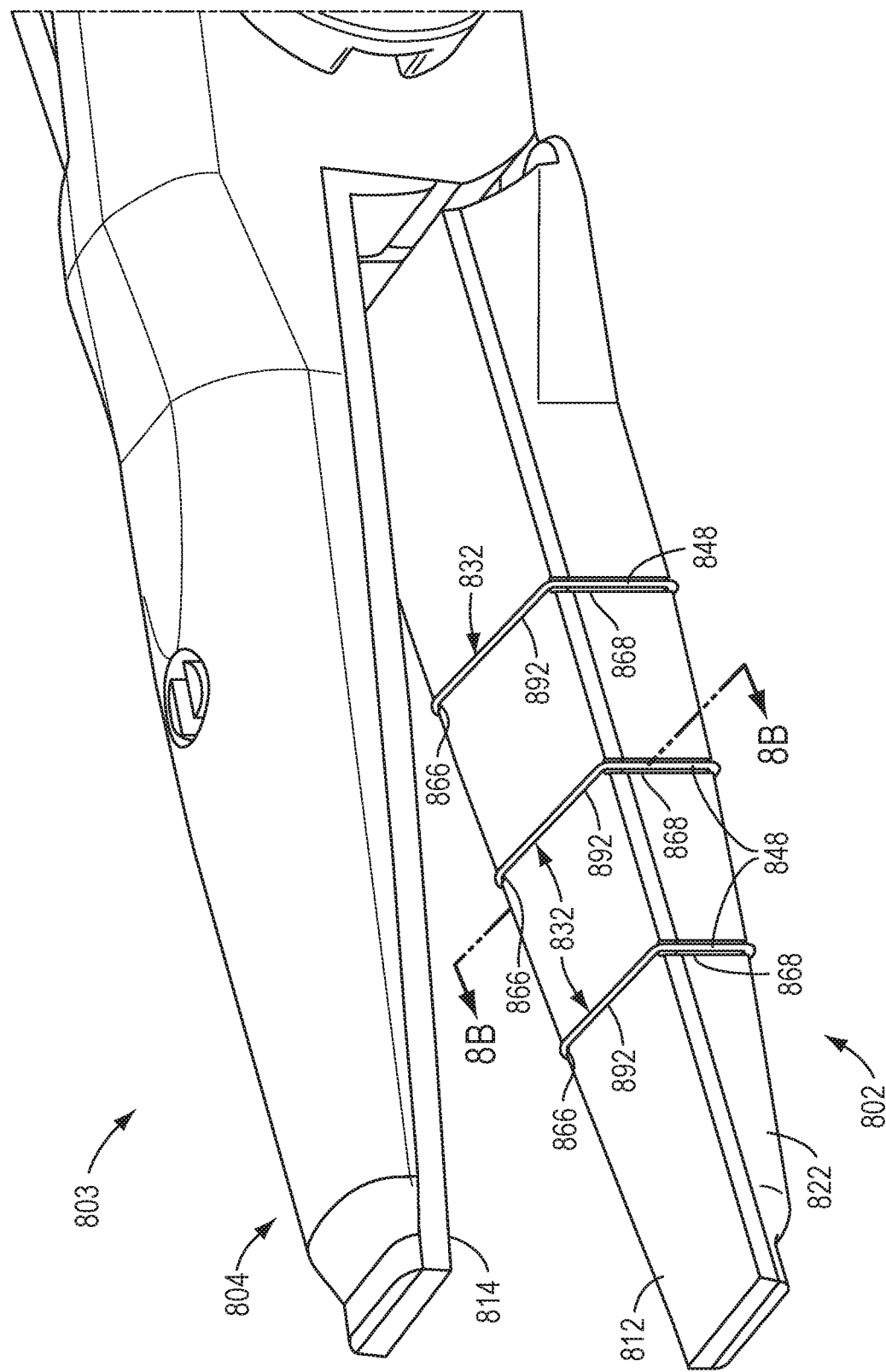
FIG. 8A is a perspective view of a pair of opposing jaw members of an end effector comprising an electrode assembly in accordance with yet another exemplary embodiment of the present disclosure.
Figure 8B:
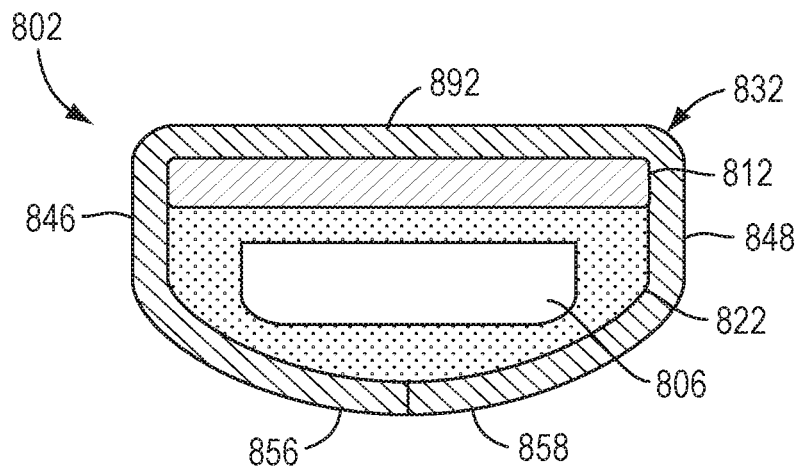
FIG. 8B is a cross-sectional view taken from 8B-8B in FIG. 8A.

Turning now to FIGS. 8A-8B, various views of an end effector in accordance with an exemplary embodiment are shown. FIG. 8A shows a perspective view of the end effector 803. FIG. 8B is a cross-sectional view of lower jaw member 802 along the 8B-8B in FIG. 8A. In the closed position (not shown) of the jaw members 802, 804, the electrodes 812, 814 of FIGS. 8A-8B are maintained spaced apart by a gap using electrode spacer filaments 832 in the form of thread disposed at intervals (which can be uniform or random) along the longitudinal length of one of the two jaw members, for example, jaw member 802. End effector 803 is an example of an embodiment of an end effector where electrode spacer filaments are only incorporated into one of the two electrode assemblies; however, persons having ordinary skill in the art would recognize that the spacer filaments also could be provided on both jaw members or on the top jaw member and not the bottom jaw member.

Each electrode spacer filament 832 comprises an exposed segment 892 that at least partially overlies the working surface of the electrode 812, a first inset segment 846, and a second inset segment 848. As shown in FIG. 8B, the exposed segment 892 extends between the first inset segment 846 and second inset segment 848. The electrode 812 and electrode support 822 can have a plurality of openings configured to receive an insulative electrode spacer filament 832 therein. The plurality of openings include a first opening 866 and a second opening 868 that serve as notched openings or grooves for retaining the insulative electrode spacer filament in place along the jaw member 802.

Each of the plurality of openings 866 and 868 is a notch formed along a side edge of the electrode that extends through the entire thickness of the electrode 812 and through the entire thickness of the electrode support 822. The first inset segment 846 extends along the thickness of the electrode 812 and electrode support 822 via a first opening 866, and likewise the second inset portion 848 segment extends along the thickness of the electrode 812 and the thickness of the electrode support 822 via a second opening 868. The first and/or second inset portions 846, 848 of the electrically insulative spacer filament 832 may be affixed to the electrode 812 and/or electrode support 822 via an adhesive, a bond, or an overmolded encapsulation. The first inset segment 846 and second inset segment 848 extend around and along the entirety of each side of jaw member 802 such that ends 856 and 858 of the first inset segment 846 and second inset segment 848 are joined and the filament 832 wraps around the entire jaw member 802 so as to bind the jaw member 802, with the notched openings 866 and 868 aiding in the retention of the insulative electrode spacer filament 832 in place. As can best be seen in FIG. 8B, the jaw body structure 806 of the jaw member 802 is completely encapsulated by the electrode support 822.

Accordingly, the electrode 812 and the electrode support 822 can be joined by virtue of the end 856 of the first inset portion 846 and the end 858 of the second inset portion 848 being affixed to on another such that the electrode spacer filament 832 binds at least the electrode 812 and the support 822 together and such binding may substantially or entirely prevent relative movement between at least the electrode 812 and the electrode support 822. Accordingly, as discussed above, spacer filaments 832 simultaneously maintain the desired gap between electrodes 812, 814 and secure the electrode 812 and electrode support 822 of an electrode assembly to each other.

Any of the thicknesses, dielectric strengths, thread formations, thread materials, and coating materials discussed above with respect to the exposed portions 392, 394, or the electrode spacers 332, 334 in general, of the exemplary embodiments of FIGS. 3A-3D, can also be applied to the exposed portions 892, or electrode spacer filaments 832 in general, of the end effector 803 shown in FIGS. 8A-8B. Accordingly, discussion of the details of the thicknesses, dielectric strengths, thread formations, thread materials, and coating materials of the spacer filaments 832 has been omitted to avoid redundancy.

Figure 9:
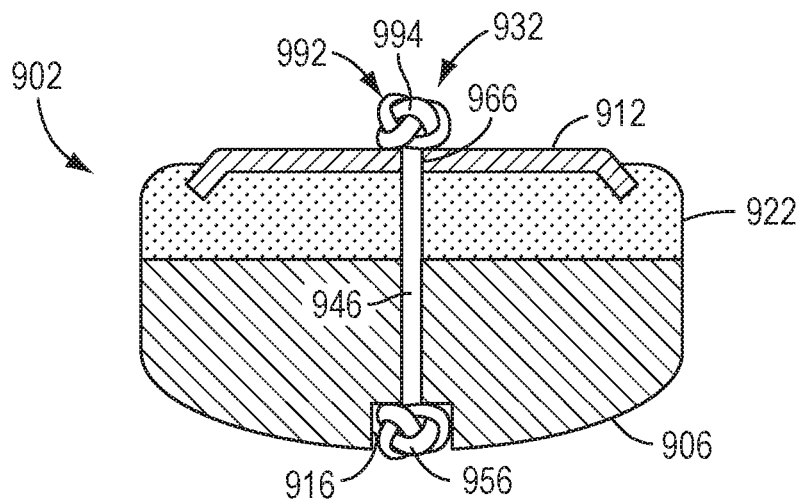
FIG. 9 is a cross-sectional view of a jaw member of an end effector comprising an electrode assembly in accordance with another exemplary embodiment of the present disclosure.

Turning now to FIG. 9, a view of a single jaw member 902 of an end effector in accordance with an exemplary embodiment are shown. FIG. 9 is a cross-sectional view of the jaw member 902. In the closed position (not shown) of jaw member 902 with an opposing jaw member (not shown), the electrodes 912 of jaw member 902 and the electrode of the opposing jaw member (not shown) are maintained spaced apart by a gap using electrode spacer filaments 932 in the form of thread disposed at intervals (which can be uniform or random) along the longitudinal length of one of the two jaw members, for example, jaw member 902. Although only a single filament 932 is shown in the view of FIG. 9, a person having ordinary skill would understand that a plurality of filaments 932 may be incorporated into an electrode assembly of a single jaw member 902.

Each electrode spacer filament 932 comprises an exposed segment 992 that at least partially overlies the working surface of the electrode 912, and a single inset segment 946. The electrode 912 and electrode support 922 can have a plurality of openings 966 configured to receive an inset portion 946 of an insulative electrode spacer filament 932 therein.

The single inset segment 946 can extend through and be retained in within the thickness of the electrode 912 and the electrode support 922. The inset segment end of the inset segment 946 can extend into the jaw body 906 and can be a knot 956 used to secure the filament 932. Similarly, the exposed segment 992 can be disposed on the exposed surface of the electrode and in the form of a knot 994 used to secure the filament in place. Although not shown, the inset segment end and/or exposed portion 992 may be additionally or solely affixed to the jaw body 906 via a bond, adhesive, and/or an encapsulation that results from overmolding. Additionally, jaw body 906 may have a recess 916 that is open such that the knot 994, 956 are accessible without having to disassemble the jaw body 906 from the components of the electrode assembly.

Figure 10:
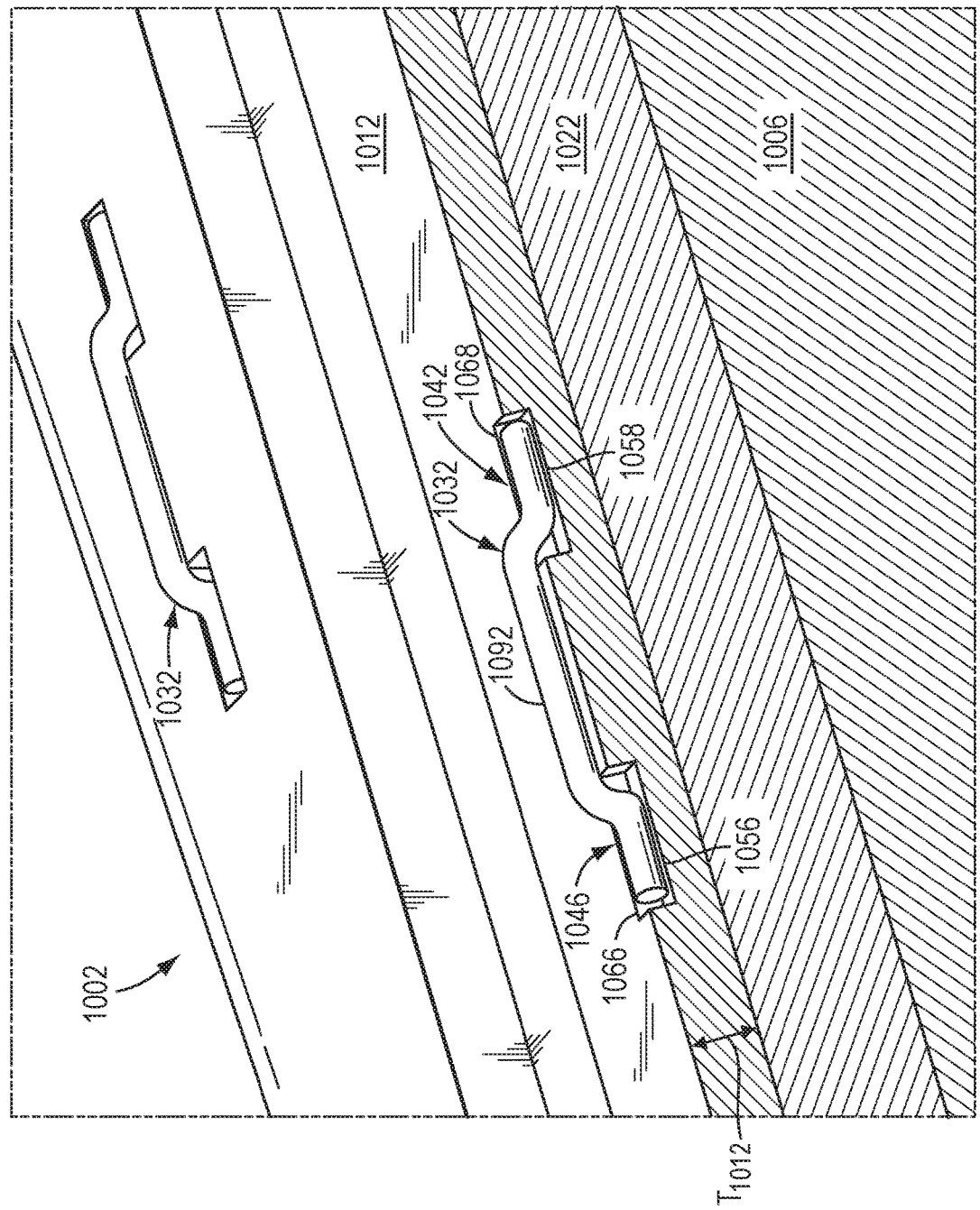
FIG. 10 is a detailed side perspective view of a single jaw member (similar to the views of FIGS. 3D, 4D, and 5D) of an end effector comprising an electrode assembly in accordance with another exemplary embodiment of the present disclosure.

Turning now to FIG. 10, a detailed side perspective view of a single jaw member 1002 of an end effector in accordance with an exemplary embodiment are shown. In the closed position of jaw member 1002 with an opposing jaw member (not shown), the electrodes 1012 of jaw member 1002 and the electrode of the opposing jaw member (not shown) are maintained spaced apart by a gap using one or more electrode spacer filaments 1032 in the form of threads, which can be disposed at intervals (uniformly or randomly) along the longitudinal length of one or both opposing jaw members, for example, jaw member 1002.

The or each electrode spacer 1032 comprises an exposed segment 1092 that at least partially overlies the working surface of the electrode 1012, and two inset segments 1046, 1048 separated by the exposed segment 1092. As shown in FIG. 10, the exposed segment 1092 extends between the first inset segment 1046 and second inset segment 1048. The electrode 1012 has a plurality of openings configured to receive and stitch an insulative electrode spacer filament 1032. The plurality of openings can include a first opening 1066 and a second opening 1068.

The first inset segment 1046 can be retained in a part of the thickness $T_{1012}$ of the electrode 1012. Accordingly, in such an exemplary embodiment, the openings 1066 and 1068 are depressions in the electrode, rather than through holes, such that the openings 1066, 1068 do not extend into the electrode support 1022 or the jaw body 1006. The first inset segment end 1056 and second inset segment end 1058 can be retained in the depression openings 1066 and 1068 via a bond and/or adhesive. Although not shown, the first and second inset segment ends may be additionally or solely affixed to electrode 1012 via a tie, knot, and/or an encapsulation that results from overmolding.

Figure 11:
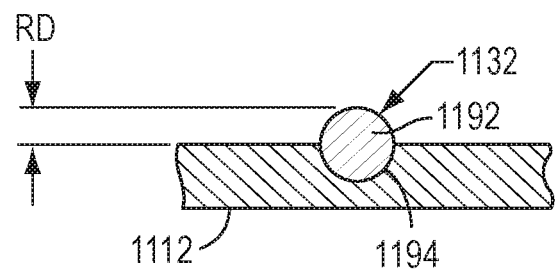
FIG. 11 is a cross-sectional view of an isolated electrode and electrode spacer filament of an exemplary electrode assembly in accordance with another exemplary embodiment of the present disclosure.

Turning now to FIG. 11, a partial, cross-sectional view of an electrode 1112 and electrode spacer filament 1132 of an exemplary electrode assembly is shown. Other additional components of the electrode assembly have been omitted for clarity. The cross-section shown in FIG. 11 is taken laterally across the exposed segment 1192 of the electrode spacer filament 1132. The surface of the electrode 1112 has a groove 1194. The exposed segment 1192 and the groove 1194 are sized relative to one another such that a portion of the exposed segment 1192 extends a raised distance RD beyond the surface of the electrode 1112. In some exemplary embodiments, the groove 1194 has a depth that ranges from about 0.003 inches to about 0.005 inches, and the exposed segment 1192 of the electrode spacer filament has a loaded thickness (i.e., a thickness of the filament spacer when under the load of closed jaw members) that ranges from about 0.006 inches to about 0.008 inches such that the raised distance RD (which defines the gap between closed jaw members) may range from about 0.001 inches to about 0.005 inches. For example, in an exemplary embodiment, the groove 1194 has a depth of about 0.004 inches, and the exposed segment 1192 of the electrode spacer filament has a loaded thickness of about 0.007 inches such that the raised distance RD (which defines the gap between closed jaw members) is about 0.003 inches. The above-described dimensions may be applied to any of the electrode assemblies in accordance with exemplary embodiments described herein.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

The nature of information depicted in the figures and described herein is exemplary. Those persons having skilled in the art would appreciate modifications to the electrode spacers and electrode assemblies can be made, such as for example, modifications to structure, dimensions, materials, and methodologies may be made without departing from the scope of the present disclosure.

It is to be understood that the particular examples and embodiments set forth herein are nonlimiting, and modifications to structure, dimensions, materials, and methodologies may be made without departing from the scope of the present disclosure and claims including equivalents.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents.

What is claimed is:

1. An electrode assembly comprising:
    an electrode support;
    an electrode on the electrode support, the electrode having a working surface extending generally transverse to a thickness of the electrode; and
    a filament of electrically insulative material overlying a portion of the working surface of the electrode and at least partially extending through the thickness of the electrode;
    wherein the filament comprises a thread.

2. The electrode assembly of claim 1 further comprising a plurality of openings each extending at least partially through the thickness of the electrode.

3. The electrode assembly of claim 2, wherein the filament comprises:
a first inset segment at least partially extending into the thickness of the electrode via a first opening of the plurality of openings; and
an exposed segment overlying the working surface of the electrode.

4. The electrode assembly of claim 3, wherein at least the exposed segment of the filament has a dielectric strength of at least 50 V/mil.

5. The electrode assembly of claim 3, wherein at least the exposed segment of the filament has a dielectric strength of at least 200 V/mil.

6. The electrode assembly of claim 3, wherein:
the filament is stitched through at least a second opening of the plurality of openings;
the filament further comprises a second inset segment extending into the thickness of the electrode via the second opening; and
the exposed segment extends between the first inset segment and second inset segment.

7. The electrode assembly of claim 6, wherein:
the first and second openings each extend through the entire thickness of the electrode and into a thickness of the electrode support;
the first inset segment extends through the entire thickness of the electrode and into the electrode support via the first opening; and
the second inset segment extends through the entire thickness of the electrode and into the electrode support via the second opening.

8. The electrode assembly of claim 7, wherein:
the first and second inset segments of the filament are each affixed to one or both of the electrode support and a jaw body; and
by virtue of the first and second inset segments each being affixed to one or both of the electrode support and the jaw body, the electrode and the electrode support are joined such that relative movement between the electrode and the electrode support is substantially or entirely prevented.

9. The electrode assembly of claim 8, wherein the first and second inset segments of the filament are each affixed to the electrode support via a tie, a knot, an adhesive, a bond, and/or an overmolded encapsulation.

10. The electrode assembly of claim 1, wherein the thread comprises an electrically insulative coating.

11. The electrode assembly of claim 1, wherein the thread comprises electrically insulative fibers.

12. The electrode assembly of claim 11, wherein the electrically insulative fibers comprise aramid fibers.

13. An electrosurgical instrument, comprising:
a shaft;
an end effector operably coupled to the shaft, the end effector comprising a pair of opposing jaw members, each jaw member comprising an electrode assembly disposed to face the electrode assembly of the opposing jaw member, wherein at least one electrode assembly comprises:
an electrode support supported by a body of the respective jaw member;
an electrode on the electrode support, the electrode having a working surface extending generally transverse to a thickness of the electrode; and
a filament of electrically insulative material overlying a portion of the working surface of the electrode and at least partially extending through the thickness of the electrode;
wherein the filament comprises a thread.

14. The electrosurgical instrument of claim 13, wherein the electrode assembly further comprises a plurality of openings each at least partially extending through the thickness of the electrode.

15. The electrosurgical instrument of claim 14, wherein each of the plurality of openings is a through hole, notch, cut out, slot, or depression.

16. The electrosurgical instrument of claim 14, wherein the filament comprises:
a first inset segment at least partially extending into the thickness of the electrode via a first opening of the plurality of openings; and
an exposed segment overlying the working surface of the electrode.

17. The electrosurgical instrument of claim 16, wherein:
the filament is stitched through at least a second opening of the plurality of openings;
the filament further comprises a second inset segment extending into the thickness of the electrode via the second opening; and
the exposed segment extends between the first inset segment and second inset segment.

18. The electrosurgical instrument of claim 17, wherein:
the first and second openings each extend through the entire thickness of the electrode and at least partially into a thickness of the electrode support;
the first inset segment extends through the entire thickness of the electrode and into the electrode support via the first opening; and
the second inset segment extends through the entire thickness of the electrode and into the electrode support via the second opening.

19. The electrosurgical instrument of claim 18, wherein:
the first and second inset segments of the filament are each affixed to the electrode support or a body of the respective jaw member, the filament with the affixed first and second inset segment securing the electrode and the electrode support to one another.

* * * * *